(12) United States Patent
Sarshar

(10) Patent No.: US 7,468,462 B2
(45) Date of Patent: Dec. 23, 2008

(54) THERAPEUTIC AGENTS FOR THE TREATMENT OF CANCER, METABOLIC DISEASES AND SKIN DISORDERS

(75) Inventor: Sepehr Sarshar, Cardiff by the Sea, CA (US)

(73) Assignee: Auspex Pharmaceuticals, Vista, CA (US)

( * ) Notice: Subject to any disclaimer, the term of this patent is extended or adjusted under 35 U.S.C. 154(b) by 0 days.

(21) Appl. No.: 11/592,009

(22) Filed: Nov. 1, 2006

(65) Prior Publication Data

US 2007/0078189 A1  Apr. 5, 2007

Related U.S. Application Data

(63) Continuation-in-part of application No. PCT/US2005/015366, filed on May 2, 2005.

(60) Provisional application No. 60/567,965, filed on May 3, 2004.

(51) Int. Cl.
*C07C 45/00* (2006.01)
*C07D 319/06* (2006.01)
*C07D 305/00* (2006.01)

(52) U.S. Cl. .................. 568/314; 549/374; 549/510

(58) Field of Classification Search ............... 549/374, 549/510; 568/341, 326, 328
See application file for complete search history.

(56) References Cited

U.S. PATENT DOCUMENTS

| 6,825,233 | B2 | 11/2004 | Ericsson et al. | 514/544 |
| 6,844,466 | B2 | 1/2005 | Belloni et al. | 562/439 |

OTHER PUBLICATIONS

Pirrung et al. STN Accession No. 1995:466019; Document No. 123:169582; Abstract of Journal of Organic Chemistry, 1995, 60(7), 2112-24.*
Okajima et al. STN Accession No. 1990:497481: Document No. 113:97481; Abstract of Journal of Heterocyclic Chemistry, 1990, 567-574.*
Winternitz et al. STN Accession No. 1950:14863; Document No. 44:14863; Abstract of Bulletin de la Societe Chimique de France (1949) 713-722.*
Rolewski S. Wikipedia, Abstact of "Clinical review: topical retinoids". Dermatol Nurs 15 (5): 447-50, 459-65, 2003.*
Muccio et al., "Conformationally Defined 6-*s*-trans-Retinoic Acid Analogs. 3. Structure-Activity Relationship for Nuclear Receptor Binding, Transcriptional Activity, and Cancer Chemopreventive Activity," *J. Med. Chem.*, 39:3625-3635, American Chemical Society (1996).
Zacheis et al., "Heteroarotinoids Inhibit head and Neck Cancer Cell Lines in Vitro and in Vivo through Both RAR and RXR Retinoic Acid Receptors," *J. med. Chem.*, 42:4434-4445, American Chemical Society (1999).

* cited by examiner

*Primary Examiner*—D. Margaret Seaman
*Assistant Examiner*—Nizal S Chandrakumar
(74) *Attorney, Agent, or Firm*—Dennis A. Bennett; Michael Sertie

(57) ABSTRACT

The present invention is directed to novel compounds according to formulae

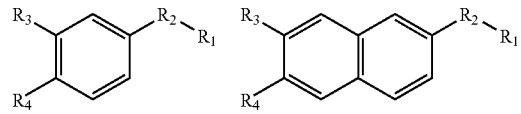

wherein $R_1$, $R_2$, $R_3$ and $R_4$ are as defined herein. The invention also discloses methods of preparation, pharmaceutical compositions, and methods of disease treatment utilizing pharmaceutical compositions comprising these compounds. The compounds of this invention are novel therapeutic agents for the treatment of cancer, diabetes, metabolic diseases and skin disorders in mammalian subjects. These compounds are also useful modulators of gene expression. They exert their activity by interfering with certain cellular signal transduction cascades. The compounds of the invention are thus also useful for regulating cell differentiation and cell cycle processes that are controlled or regulated by various hormones or cytokines. The invention also discloses pharmaceutical compositions and methods of treatment of disease in mammals.

7 Claims, 5 Drawing Sheets

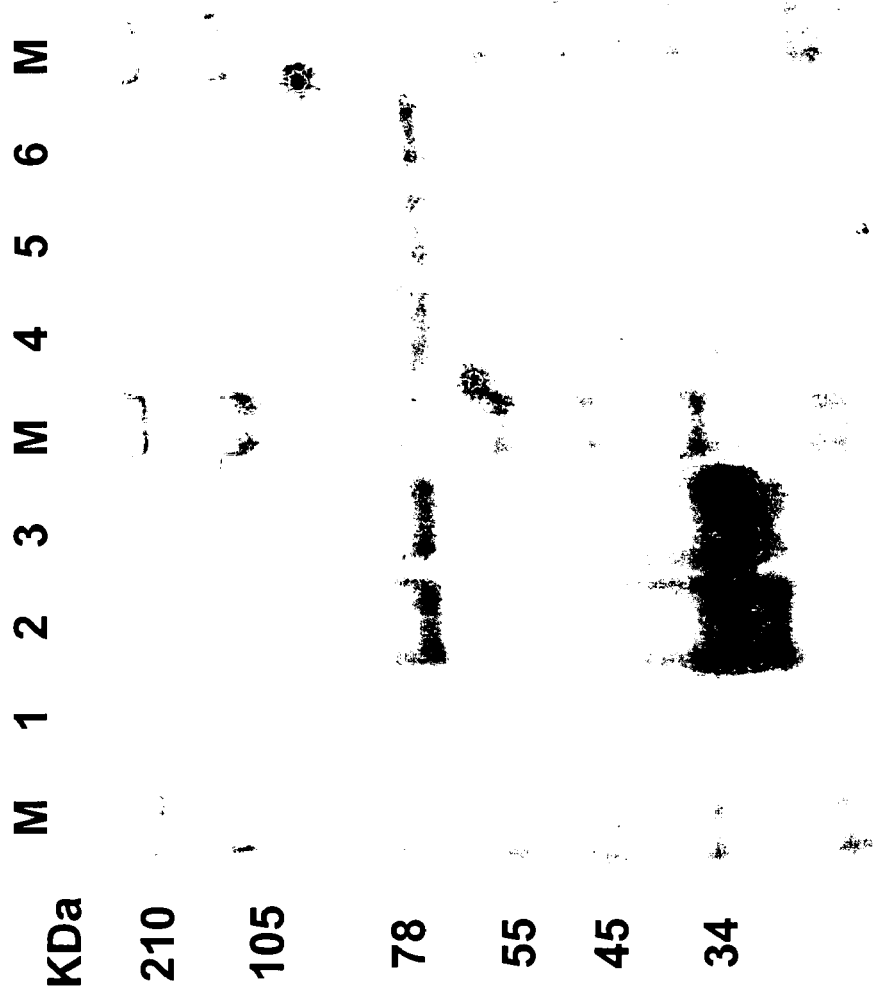
Figure 1. Electrophoretically separated fractions 1-6 with marker for purified RAR-alpha

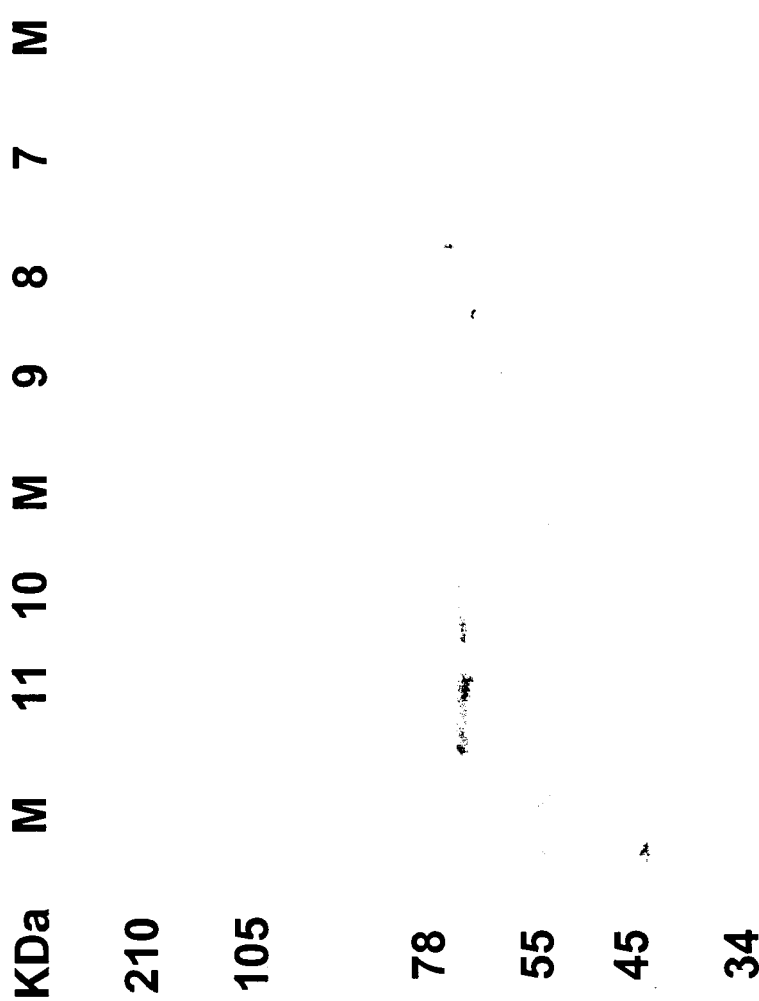
Figure 2. Electrophoretically separated fractions 7-11 with marker for purified RAR-alpha

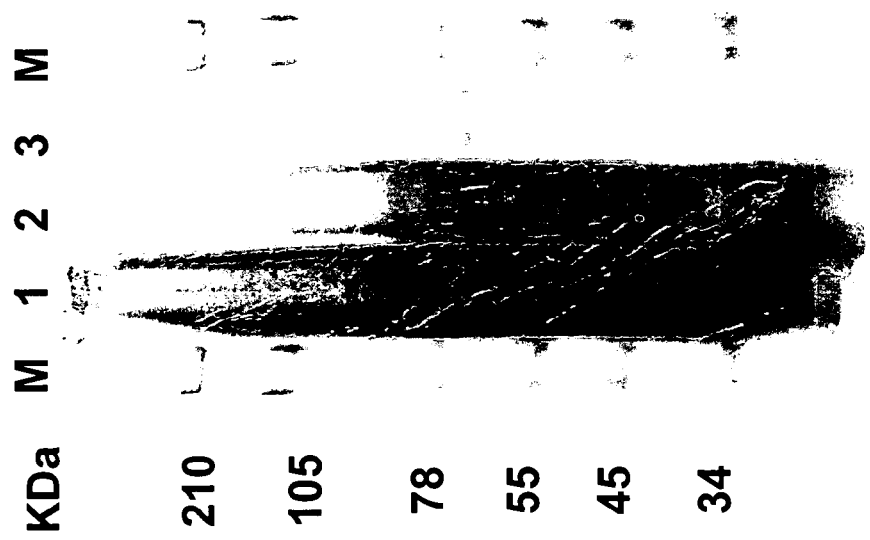
Figure 3. Lane 1 - Electrophoretically separated bacterial sonicate
Lane 2 - Electrophoretically separated supernatant after centrifuge
Lane 3 - Electrophoretically separated pooled fractions 4-11

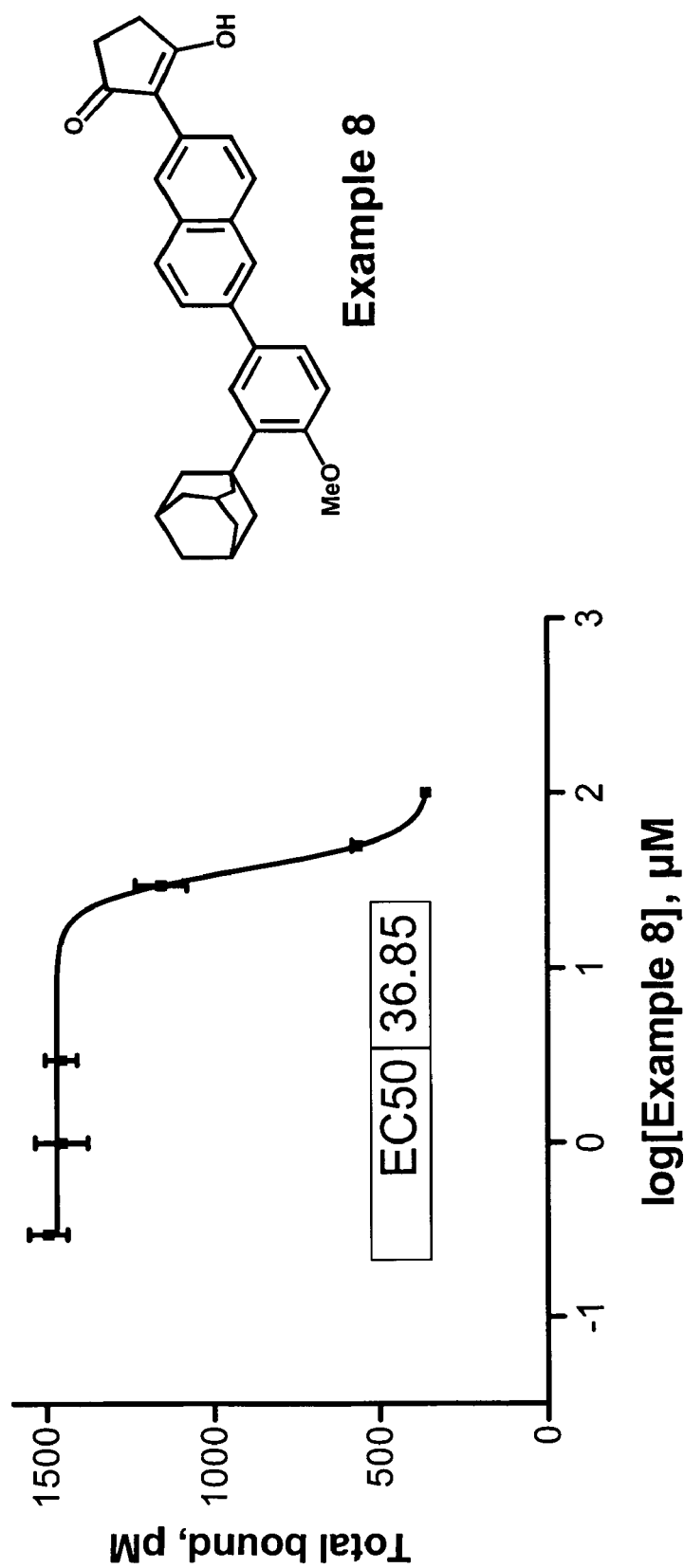
Figure 4. EC$_{50}$ for example 8 in RAR-alpha radioligand binding assay

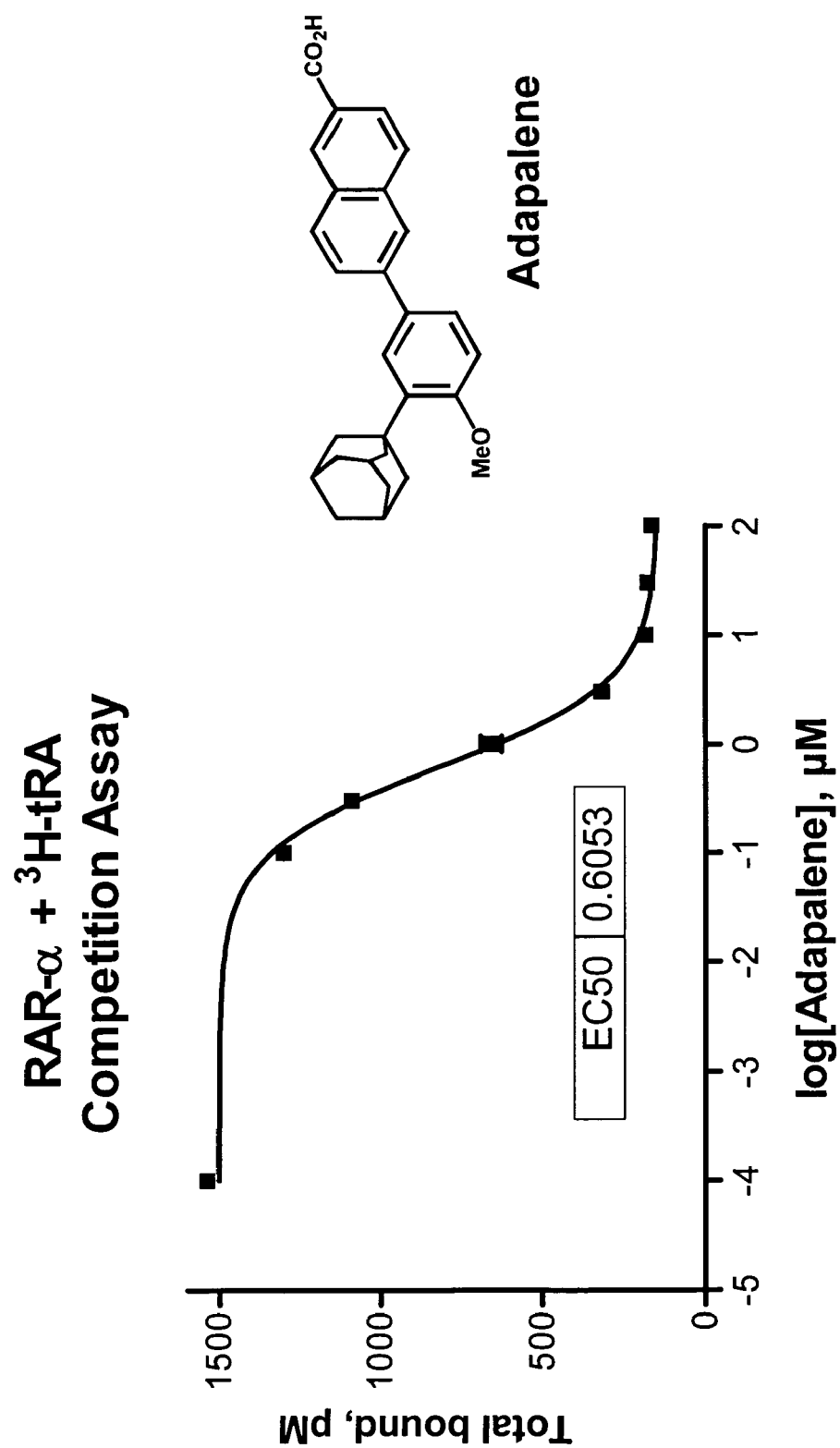
Figure 5. $EC_{50}$ for adapalene in RAR-alpha radioligand binding assay

THERAPEUTIC AGENTS FOR THE TREATMENT OF CANCER, METABOLIC DISEASES AND SKIN DISORDERS

CROSS REFERENCE TO RELATED APPLICATIONS

Under 35 USC § 120, this is a Continuation-in-Part application of PCT Application No. PCT/US2005/015366 filed May 2, 2005, which claims the benefit under 35 USC § 119(e) to U.S. application Ser. No. 60/567,965 filed May 3, 2004. The disclosure of the prior applications is considered part of and is incorporated by reference in the disclosure of this application.

FIELD OF THE INVENTION

The compounds of this invention are novel therapeutic agents for the treatment of cancer, metabolic diseases and skin disorders in mammalian subjects.

BACKGROUND OF THE INVENTION

Retinoids, natural and synthetic analogues of vitamin A, play a major role in controlling cell proliferation, differentiation, embryonic development and apoptosis. All-trans-Retinoic acid (AtRA), 13-cis-retinoic acid, and synthetic analogues are widely used for topical and oral administration in the management of dermatological diseases such as acne, psoriasis, and other disorders in which abnormal patterns of keratinization are found. Many biological effects of retinoids are mediated by the activation of a family of gene transcription factors known as Retinoic Acid Receptors (RARs) and Retinoid X Receptors (RXRs). Each class is composed of three distinct receptor subtypes ($\alpha$, $\beta$ and $\gamma$). After complexation with a ligand, RARs exert their gene transcriptional activity by forming a heterodimer with Retinoid X Receptors (RXRs). Side effects such as mucocutaneous irritation, hypervitaminosis A, and teratogenicity are drawbacks in the therapeutic use of retinoids.

The discovery of RAR and RXR subtypes has stimulated medicinal chemists to seek novel subtype-selective drugs with improved therapeutic indices. In normal skin, RAR-$\alpha$ and predominantly RAR-$\gamma$ are present in the keratinocytes of the epidermis. RAR-$\beta$ is neither expressed nor induced in this skin layer. In contrast, in the dermis, the fibroblast does express RAR-$\beta$ and in addition the gene encoding RAR-$\beta$ is also inducible by retinoic acid in this cell type. Consequently, in the field of dermatology, selective compounds for the RAR-$\gamma$ subtype act preferentially in the epidermis, while RAR-$\beta$ mediated action leads to response in fibroblasts; therefore, for skin disorders that involve the RAR signaling pathway, molecules with mixed RAR-$\beta$/$\gamma$ profiles are preferred.

Cancer is a complex disease characterized by genetic mutations that lead to uncontrolled cell growth. Cancerous cells are present in all organisms and under normal circumstances their excessive growth is tightly regulated by various physiological factors. One such regulatory process is apoptosis or programmed cell death. When the internal machinery of a cell detects abnormalities in cell division and growth, a signal is propagated within the cell, activating suicide proteins that kill the afflicted cell and prevent its proliferation. Such an apoptotic signal can be triggered, for example, when a ligand or drug interacts with a receptor or protein in the cell.

Most agents that induce apoptosis in cancer cells (e.g. Doxorubicin and Vincristine) are extremely toxic and cause a number of undesirable side effects. The toxicity associated with these therapies is a result of the non-specific interaction of the drug with the DNA of non-cancerous cells (e.g. intestinal and red blood cells). In order to circumvent such undesirable side effects, more selective compounds have been designed that inhibit one or more signaling proteins, growth factors and/or receptors involved in cancer cell proliferation. Examples include monoclonal antibodies for breast cancer (e.g. Herceptin) and Non-Hodgkin's Lymphoma (e.g. Rituxan), as well anti-angiogenic drugs for chronic myeloid leukemia (e.g. Gleevec). Since patient populations are genetically heterogeneous, it follows that a single selective therapy will not work in all cases, and as a result, cancer drugs are often used in combination. As such, there is a continual need for improved treatments.

Clinical studies have shown that retinoic acid and its synthetic analogs can inhibit the growth and invasion of cancer cells, and induce them to undergo apoptosis, thereby eradicating various types of cancers.

The novel compounds of this invention modulate the activity of Nuclear Retinoid receptors. These novel compounds are thus useful for regulating cell differentiation and cell cycle processes as well as other cellular signaling processes controlled or regulated by hormones and vitamins such as the thyroid hormone, vitamin D, all-trans retinoic acid and 9-cis-retinoic acid. Hence, conditions and/or diseases that are regulated by the aforementioned entities may be treated using the compounds of this invention. Examples of such conditions include for example cancer, mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia, acne, psoriasis, aging, wrinkling, diabetes, hyperglycemia, bone calcification, thyroid conditions, and the like.

Compounds that modulate the activity of RAR receptors are structural analogs of all-trans-retinoic acid. On the other hand compounds that modulate the activity of RXR receptors are structural analogs of 9-cis-retinoic acid (e.g. Bexarotene). The aforementioned modulators of Nuclear Retinoid receptors bear a carboxylic acid group in a specific position of the molecule. This acidic group forms a salt bridge to a basic residue in the binding pocket of the Nuclear Retinoid receptors. Research in this field indicates that removal of this acidic group drastically reduces the potency or the modulator. There are however, other amino acid residues in the binding pocket that can interact with the modulator. None of the modulators of Nuclear Retinoid receptors described to date take advantage of these critical interactions.

Another drawback of the current state of the art is the limited aqueous solubility of the selective Nuclear Retinoid receptor modulators. Said modulators mimic the structures of retinoic acids in order to conform to the three-dimensional structure and the hydrophobic nature of the respective binding pockets. In general, introduction of solubilizing substituents has resulted in lower in vitro binding affinity or increased in vivo metabolism and toxicity.

For treatment of skin disorders such as acne and psoriasis, agents are needed that can help alleviate the symptoms of the disorders without irritating the skin. Another drawback of the current state of the art is the low pKa of the carboxylic acid residue present in the selective Nuclear Retinoid receptor modulators. When applied topically, this acidic residue can lower the pH of the skin and in turn cause redness and irritation of the dermis.

There exists therefore a need to improve upon the prior art in order to enhance the clinical profile of such therapeutics. Such improvements may be carried out by introducing specially designed functional groups at specific positions on the molecular backbone of the modulator. The novel compounds of this invention address this issue and display enhanced in vitro profiles when compared to compounds of the prior art.

SUMMARY OF THE INVENTION

This invention provides novel therapeutic agents for the treatment of cancer, metabolic diseases and skin disorders in mammalian subjects. These agents bear specially designed functional groups at specific positions on the molecular backbone of the modulator. These modifications provide additional interactions between the compounds of this invention and certain amino acid residues in the binding pocket of the Retinoid Nuclear receptors.

The invention also provides compounds that interact with one or more cellular receptors and are useful in the modulation of gene expression.

Furthermore, the invention also provides compounds that are useful in controlling cell cycle, and cell differentiation processes regulated by certain hormones, such as for example the thyroid hormone and the like, and/or certain vitamins, such as for example vitamin D and the like, and/or certain retinoids, such as for example 9-cis-retinoic acid and the like.

Furthermore, the invention also provides compounds that are useful in inducing apoptosis in mammalian cells.

Furthermore, the invention also provides compounds that are useful in treating skin disorders in mammalian subjects.

Furthermore, the invention also provides chemical compositions and discloses synthetic methodologies to prepare the same.

In one aspect, the invention relates to compounds having the structural formula:

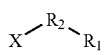

wherein:

X is selected from a group consisting of the structural formulae $A_1$ and $A_2$

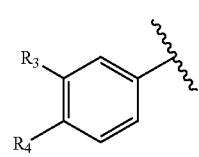

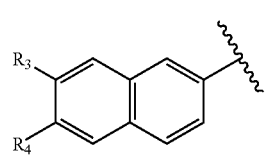

$R_1$ is selected from a group consisting of the structural formulae $B_1$, $B_2$, and $B_3$,

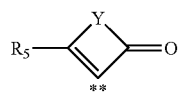

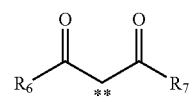

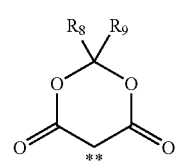

$R_2$ is selected from a group consisting of aryl and heteroaryl, with the proviso that if $R_2$ is a substituted phenyl, then $R_1$ and X cannot be meta to each other and if $R_2$ is phenyl or a substituted phenyl, $R_6$ and $R_7$ cannot both be methyl.

$R_3$ is selected from a group consisting of hydrogen, alkyl, adamantyl, alkyloxy, alkylthio, halogen, aryl, aryloxy, arylthio, and heteroaryl;

$R_4$ is selected from a group consisting of hydrogen, hydroxy, alkyl, alkyloxy, alkylthio, aryl, aryloxy, arylthio and heteroaryl; or $R_3$ and $R_4$ may be linked together to form a substituted or unsubstituted 5- or 6-membered cycloalkyl or cycloalkenyl ring, where said substituents are selected from a group consisting of —OH, =O, halogen, and alkyl, and where one of the carbon atoms on said 5- or 6-membered cycloalkyl or cycloalkenyl ring may be optionally replaced by W where W is selected from a group consisting of O, S, N, NH, alkylamino, and arylamino;

$R_5$, $R_6$ and $R_7$ are independently selected from a group consisting of —OH, alkyl, aryl, alkyloxy, aryloxy, —NH$_2$, alkylamino, arylamino, N-aryl-N-alkylamino, —NHNH$_2$, alkylhydrazino, arylhydrazino, N-aryl-N-alkylhydrazino, and —NHOR$_8$;

$R_8$ and $R_9$ are independently selected from a group consisting of hydrogen, alkyl, and aryl;

Y is selected from a group consisting of $C_{2-8}$ alkyl, and $C_{2-8}$ substituted alkyl;

** represents the point of attachment of $R_1$ to $R_2$ and pharmaceutically acceptable salts thereof.

The non-limiting examples shown in schemes 1-2, illustrate some methods for carrying out the preparative process of the invention. PG represents a hydroxyl protecting group as defined herein, and R is selected from a group consisting of alkyl, and aryl.

Scheme 1

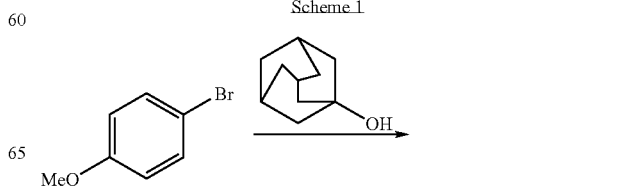

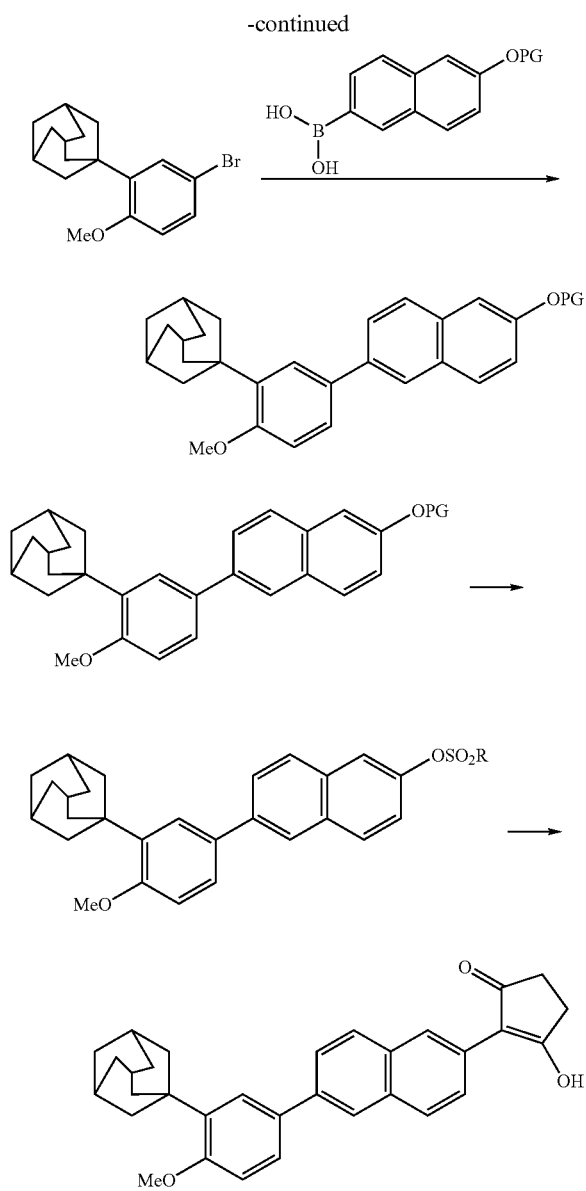

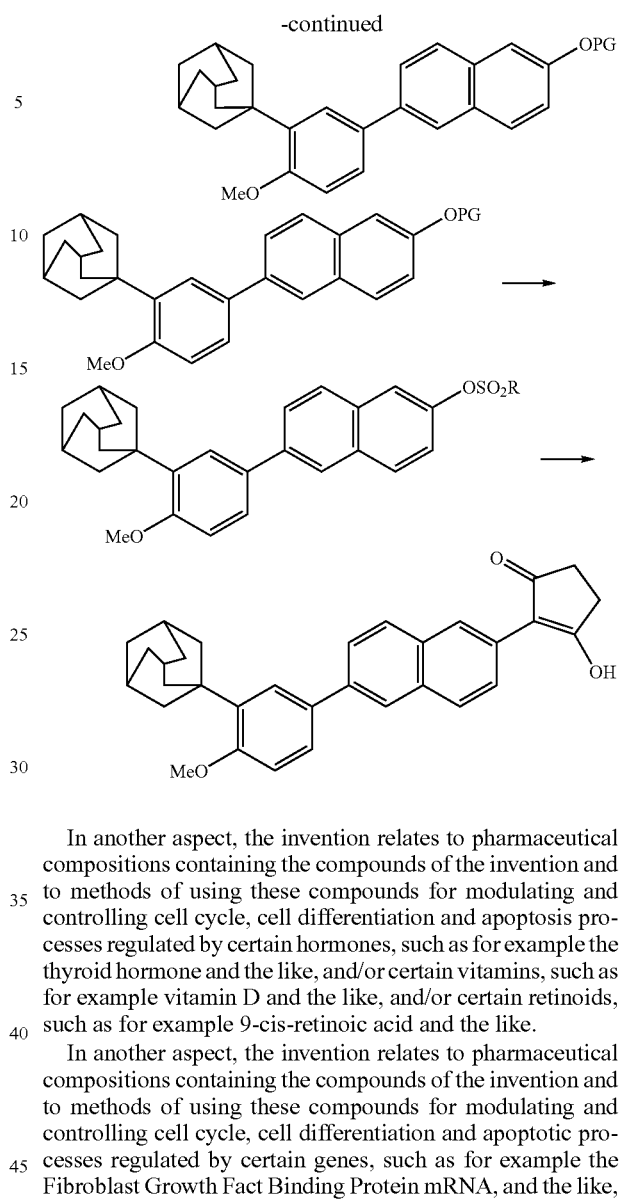

Scheme 2

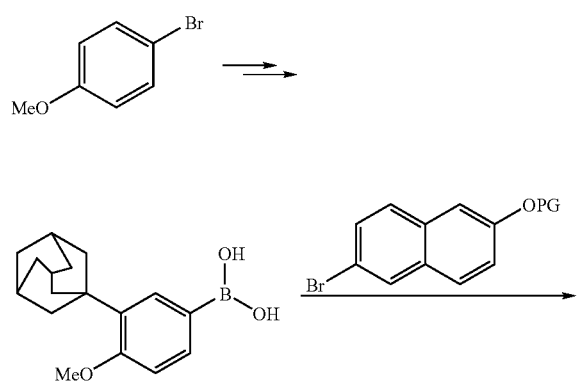

In another aspect, the invention relates to pharmaceutical compositions containing the compounds of the invention and to methods of using these compounds for modulating and controlling cell cycle, cell differentiation and apoptosis processes regulated by certain hormones, such as for example the thyroid hormone and the like, and/or certain vitamins, such as for example vitamin D and the like, and/or certain retinoids, such as for example 9-cis-retinoic acid and the like.

In another aspect, the invention relates to pharmaceutical compositions containing the compounds of the invention and to methods of using these compounds for modulating and controlling cell cycle, cell differentiation and apoptotic processes regulated by certain genes, such as for example the Fibroblast Growth Fact Binding Protein mRNA, and the like, and/or certain Signal Transducers and Activators of Transcription, such as for example STAT3, and the like, and/or certain proteins, such as for example Cyclin Dependent Kinase (CDK), Transforming Growth Factor alpha (TGF-α), and the like, and/or certain receptors, such as for example Transforming Growth Factor Receptor (TGFR), Endothelial Growth Factor Receptor (EGFR), Retinoid X Receptor (RXR) and the like.

In another aspect, the invention relates to pharmaceutical compositions containing the compounds of the invention and to methods of using these compounds to modulate selective gene expression by one or more cellular receptors.

In another aspect, the invention relates to pharmaceutical compositions containing the compounds of the invention and to methods of treating diseases and/or conditions using the same. Examples of such disorders include proliferative disorders, differentiation disorders, cancer, mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia, diabetes, inflammatory diseases, cardiovascular diseases, plasma HDL levels, apolipoprotein A1 metabolism, hyperlipidemia, lipid metabolism, lipid homeostasis, hyperlipidemia, skin-related processes, acne, psoriasis, aging, wrinkling, autoimmune diseases, fatty acid metabolism, malignant cell development, premalignant lesions, programmed cell death, endocrinological processes, AP-1 metabolism, hyperglycemia, bone calcification, thyroid conditions and the like.

In yet another aspect, the invention relates to pharmaceutical compositions containing the compounds of the invention in combination with other therapeutic agents and to methods of treating diseases and/or conditions using the same. Example of diseases and/or conditions include cancer, mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia and the like. Examples of other therapeutic agents include Busulfan, Carboplatin, Cisplatin, Cyclophosphamide, Cytosine arabinoside, Etoposide, 5-Fluorouracil, Melphalan, Methotrexate, Mitoxantrone, Taxol, Interferon, Fareston, Arzoxifene, Evista, Tamoxifen, and the like.

The invention further provides pharmaceutical compositions containing one or more of the compounds as well as pharmaceutically acceptable pro-drugs and salts of such compounds.

Additional features of the invention are set forth in part in the detailed description which follows.

BRIEF DESCRIPTION OF THE DRAWINGS

FIG. 1 shows the results of electrophoretic separation for some fractions of purified RAR-α.

FIG. 2 shows the results of electrophoretic separation for other fractions of purified RAR-α.

FIG. 3 shows the comparative results of electrophoretic separation for bacterial sonicate, supernatant after centrifugation, and some fractions of purified RAR-α.

FIG. 4 shows the value of $EC_{50}$ for one compound of the invention used in RAR-α radioligand binding assay.

FIG. 5 shows the value of $EC_{50}$ for a adapalene used in RAR-α radioligand binding assay.

DETAILED DESCRIPTION OF THE INVENTION

In one embodiment of the invention, there are provided compounds having the structural formula:

$$X \diagdown R_2 \diagdown R_1$$

wherein:

X is selected from a group consisting of the structural formulae $A_1$ and $A_2$

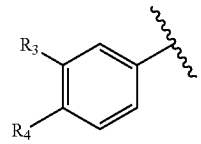

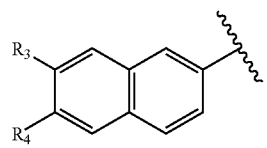

$R_1$ is selected from a group consisting of the structural formulae $B_1$, $B_2$, and $B_3$,

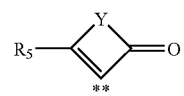

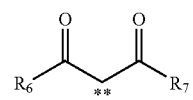

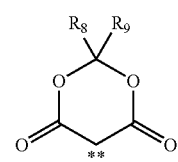

$R_2$ is selected from a group consisting of aryl and heteroaryl, with the proviso that if $R_2$ is a substituted phenyl, then $R_1$ and X cannot be meta to each other and if $R_2$ is phenyl or a substituted phenyl, $R_6$ and $R_7$ cannot both be methyl.

$R_3$ is selected from a group consisting of hydrogen, alkyl, adamantyl, alkyloxy, alkylthio, halogen, aryl, aryloxy, arylthio, and heteroaryl;

$R_4$ is selected from a group consisting of hydrogen, hydroxy, alkyl, alkyloxy, alkylthio, aryl, aryloxy, arylthio and heteroaryl; or $R_3$ and $R_4$ may be linked together to form a substituted or unsubstituted 5- or 6-membered cycloalkyl or cycloalkenyl ring, where said substituents are selected from a group consisting of —OH, =O, halogen, and alkyl, and where one of the carbon atoms on said 5- or 6-membered cycloalkyl or cycloalkenyl ring may be optionally replaced by W where W is selected from a group consisting of O, S, N, NH, alkylamino, and arylamino;

$R_5$, $R_6$ and $R_7$ are independently selected from a group consisting of —OH, alkyl, aryl, alkyloxy, aryloxy, —NH$_2$, alkylamino, arylamino, N-aryl-N-alkylamino, —NHNH$_2$, alkylhydrazino, arylhydrazino, N-aryl-N-alkylhydrazino, and —NHOR$_8$;

$R_8$ and $R_9$ are independently selected from a group consisting of hydrogen, alkyl, and aryl;

Y is selected from a group consisting of $C_{2-8}$ alkyl, and $C_{2-8}$ substituted alkyl;

** represents the point of attachment of $R_1$ to $R_2$ and pharmaceutically acceptable salts thereof.

In another embodiment of the invention, there are provided Compounds selected from a group consisting of the structural formulae $C_1$ and $C_2$:

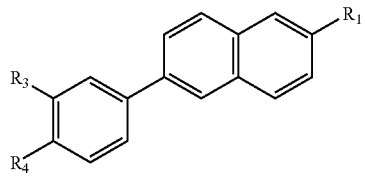

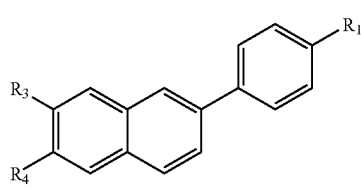

wherein $R_1$, $R_3$ and $R_4$ are as described above.

The compounds according to this invention may contain one or more asymmetric carbon atoms and can thus occur as racemates and racemic mixtures, single enantiomers, diastereomeric mixtures or individual diastereomers. The term "stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds described herein may have one or more asymmetrical carbon atoms and therefore include various stereoisomers. All such isomeric forms of these compounds are expressly included in the present invention.

Each stereogenic carbon may be of R or S configuration. Although the specific compounds exemplified in this application may be depicted in a particular configuration, compounds having either the opposite stereochemistry at any given chiral center or mixtures thereof are also envisioned. When chiral centers are found in the derivatives of this invention, it is to be understood that this invention encompasses all possible stereoisomers.

The terms "optically pure compound" or "optically pure isomer" refers to a single stereoisomer of a chiral compound regardless of the configuration of the said compound.

For purpose of this application, all sugars are referenced using conventional three-letter nomenclature. All sugars are assumed to be in the D-form unless otherwise noted, except for fucose, which is in the L-form. Further, all sugars are in the pyranose form.

The compounds according to this invention may occur as a mixture of tautomers. The term "tautomer" or "tautomerism" refer to one of two or more structural isomers that exist in equilibrium and are readily converted from one isomeric form to another. Examples of include keto-enol tautomers, such as acetone/propen-2-ol and the like, ring-chain tautomers, such as glucose/2,3,4,5,6-pentahydroxy-hexanal and the like. The compounds described herein may have one or more tautomers and therefore include various isomers. All such isomeric forms of these compounds are expressly included in the present invention. The following example of tautomerism is provided for reference:

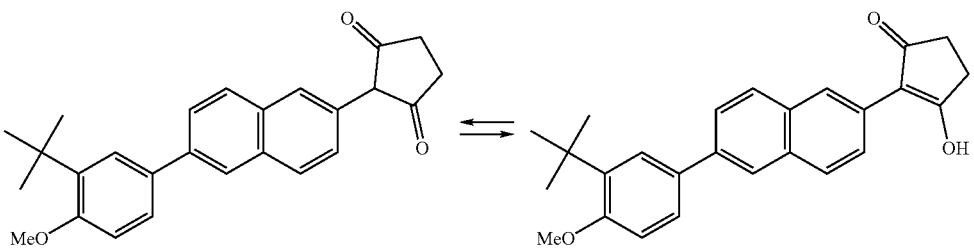

The following example of nomenclature and numbering system is provided for reference.

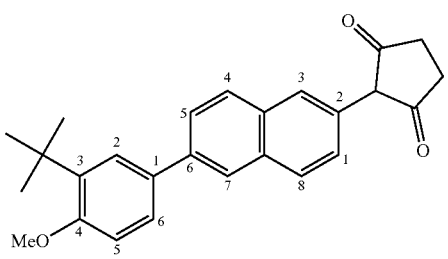

2-[6-(3-tert-Butyl-4-methoxy-phenyl)-naphthalen-2-yl]-cyclopentane-1,3-dione

The term "substantially homogeneous" refers to collections of molecules wherein at least 80%, preferably at least about 90% and more preferably at least about 95% of the molecules are a single compound or a single stereoisomer thereof.

As used herein, the term "attached" signifies a stable covalent bond, certain preferred points of attachment being apparent to those skilled in the art.

The terms "optional" or "optionally" refer to occurrence or non-occurence of the subsequently described event or circumstance, and that the description includes instances where said event or circumstance occurs and instances where it does not. In such context, the sentence "optionally substituted alkyl group" means that the alkyl group may or may not be substituted and the description includes both a substituted and an unsubstituted alkyl group.

The term "effective amount" of a compound refers a non-toxic but sufficient amount of the compound that provides a desired effect. This amount may vary from subject to subject, depending on the species, age, and physical condition of the subject, the severity of the disease that is being treated, the particular compound used, its mode of administration, and the like. Therefore, it is difficult to generalize an exact "effective amount", yet, a suitable effective amount may be determined by one of ordinary skill in the art.

The term "pharmaceutically acceptable" refers to a compound, additive or composition that is not biologically or otherwise undesirable. For example, the additive or composition may be administered to a subject along with a compound of the invention without causing any undesirable biological effects or interacting in an undesirable manner with any of the other components of the pharmaceutical composition in which it is contained.

The term "pharmaceutically acceptable salts" includes hydrochloric salt, hydrobromic salt, hydroiodic salt, hydrofluoric salt, sulfuric salt, citric salt, maleic salt, acetic salt, lactic salt, nicotinic salt, succinic salt, oxalic salt, phosphoric salt, malonic salt, salicylic salt, phenylacetic salt, stearic salt, pyridine salt, ammonium salt, piperazine salt, diethylamine salt, nicotinamide salt, formic salt, urea salt, sodium salt, potassium salt, calcium salt, magnesium salt, zinc salt, lithium salt, cinnamic salt, methylamino salt, methanesulfonic salt, picric salt, tartaric salt, triethylamino salt, dimethylamino salt, tris(hydroxymethyl)aminomethane salt and the like. Additional pharmaceutically acceptable salts are known to those of skill in the art.

When used in conjunction with a compound of this invention, the terms "elicite", "eliciting," "modulator", "modulate", "modulating", "regulator", "regulate" or "regulating" selective gene expression refer to a compound that can act as an activator, an agonist, a pan-agonist or an antagonist of gene expression by a particular receptor, such as for example a Retinoid X Receptor and the like.

The terms "therapeutic agent" and "chemotherapeutic agent", refer to a compound or compounds and pharmaceutically acceptable compositions thereof that are administered to mammalian subjects as prophylactic or remedy in the treatment of a disease or medical condition. Such compounds may be administered to the subject via oral formulation, transdermal formulation or by injection.

The term "Lewis acid" refers to a molecule that can accept an unshared pair of electrons and as such would be obvious to one of ordinary skill and knowledge in the art. The definition of "Lewis acid" includes but is not limited to: boron trifluoride, boron trifluoride etherate, boron trifluoride tetrahydrofuran complex, boron trifluoride tert-butyl-methyl ether complex, boron trifluoride dibutyl ether complex, boron trifluoride dihydrate, boron trifluoride di-acetic acid complex, boron trifluoride dimethyl sulfide complex, boron trichloride, boron trichloride dimethyl sulfide complex, boron tribromide, boron tribromide dimethyl sulfide complex, boron triiodide, triimethoxyborane, triethoxyborane, trimethylaluminum, triethylaluminum, aluminum trichloride, aluminum trichloride tetrahydrofuran complex, aluminum tribromide, titanium tetrachloride, titanium tetrabromide, titanium iodide, titanium tetraethoxide, titanium tetraisopropoxide, scandium (III) trifluoromethanesulfonate, yttrium (III) trifluoromethanesulfonate, ytterbium (III) trifluoromethanesulfonate, lanthanum (III) trifluoromethanesulfonate, zinc (II) chloride, zinc (II) bromide, zinc (II) iodide, zinc (II) trifluoromethanesulfonate, zinc (II) sulfate, magnesium sulfate, lithium perchlorate, copper (II) trifluoromethanesulfonate, copper (II) tetrafluoroborate and the like. Certain Lewis acids may have optically pure ligands attached to the electron acceptor atom, as set forth in Corey, E. J. Angewandte Chemie, International Edition (2002), 41(10), 1650-1667; Aspinall, H. C. Chemical Reviews (Washington, D.C., United States) (2002), 102(6), 1807-1850; Groger, H. Chemistry—A European Journal (2001), 7(24), 5246-5251; Davies, H. M. L. Chemtracts (2001), 14(11), 642-645; Wan, Y. Chemtracts (2001), 14(11), 610-615; Kim, Y. H. Accounts of Chemical Research (2001), 34(12), 955-962; Seebach, D. Angewandte Chemie, International Edition (2001), 40(1), 92-138; Blaser, H. U. Applied Catalysis, A: General (2001), 221(1-2), 119-143; Yet, L. Angewandte Chemie, International Edition (2001), 40(5), 875-877; Jorgensen, K. A. Angewandte Chemie, International Edition (2000), 39(20), 3558-3588; Dias, L. C. Current Organic Chemistry (2000), 4(3), 305-342; Spindler, F. Enantiomer (1999), 4(6), 557-568; Fodor, K. Enantiomer (1999), 4(6), 497-511; Shimizu, K. D.; Comprehensive Asymmetric Catalysis I-III (1999), 3, 1389-1399; Kagan, H. B. Comprehensive Asymmetric Catalysis I-III (1999), 1, 9-30; Mikami, K. Lewis Acid Reagents (1999), 93-136 and all references cited therein. Such Lewis acids maybe used by one of ordinary skill and knowledge in the art to produce optically pure compounds from achiral starting materials.

The term "acylating agent" refers to a molecule that can transfer an alkylcarbonyl, substituted alkylcarbonyl or aryl carbonyl group to another molecule. The definition of "acylating agent" includes but is not limited to ethyl acetate, vinyl acetate, vinyl propionate, vinyl butyrate, isopropenyl acetate, 1-ethoxyvinyl acetate, trichloroethyl butyrate, trifluoroethyl butyrate, trifluoroethyl laureate, S-ethyl thiooctanoate, biacetyl monooxime acetate, acetic anhydride, acetyl chloride, succinic anhydride, diketene, diallyl carbonate, carbonic acid but-3-enyl ester cyanomethyl ester, amino acid and the like.

The term "nucleophile" or "nucleophilic reagent" refers to a negatively charged or neutral molecule that has an unshared pair of electrons and as such would be obvious to one of ordinary skill and knowledge in the art. The definition of "nucleophile" includes but is not limited to: water, alkylhydroxy, alkoxy anion, arylhydroxy, aryloxy anion, alkylthiol, alkylthio anion, arylthiol, arylthio anion, ammonia, alkylamine, arylamine, alkylamine anion, arylamine anion, hydrazine, alkyl hydrazine, arylhydrazine, alkylcarbonyl hydrazine, arylcarbonyl hydrazine, hydrazine anion, alkyl hydrazine anion, arylhydrazine anion, alkylcarbonyl hydrazine anion, arylcarbonyl hydrazine anion, cyanide, azide, hydride, alkyl anion, aryl anion and the like.

The term "electrophile" or "electrophilic reagent" refers to a positively charged or neutral molecule that has an open valence shell and as such would be obvious to one of ordinary skill and knowledge in the art. The definition of "electrophile" includes but is not limited to: hydronium, acylium, lewis acids, such as for example, boron trifluoride and the like, halogens, such as for example $Br_2$ and the like, carbocations, such as for example tert-butyl cation and the like, diazomethane, trimethylsilyldiazomethane, alkyl halides, such as for example methyl iodide, benzyl bromide and the like, alkyl triflates, such as for example methyl triflate and the like, alkyl sulfonates, such as for example ethyl toluenesulfonate, butyl methanesulfonate and the like, acyl halides, such as for example acetyl chloride, benzoyl bromide and the like, acid anhydrides, such as for example acetic anhydride, succinic anhydride, maleic anhydride and the like, isocyanates, such as for example methyl isocyanate, phenylisocyanate and the like, chloroformates, such as for example methyl chloroformate, ethyl chloroformate, benzyl chloroformate and the like, sulfonyl halides, such as for example methanesulfonyl chloride, p-tolunesulfonyl chloride and the like, silyl halides, such as for example trimethylsilyl chloride, tertbutyldimethyl silyl chloride and the like, phosphoryl halide such as for example dimethyl chlorophosphate and the like, alpha-beta-unsaturated carbonyl compounds such as for example acrolein, methyl vinyl ketone, cinnamaldehyde and the like.

The term "leaving group" refers to any atom (or group of atoms) that is stable in its anion or neutral form after it has been displaced by a nucleophile and as such would be obvious to one of ordinary skill and knowledge in the art. The definition of "leaving group" includes but is not limited to: water, methanol, ethanol, chloride, bromide, iodide, methanesulfonate, tolylsulfonate, trifluoromethanesulfonate, acetate, trichloroacetate, benzoate and the like.

The term "oxidant" refers to any reagent that will increase the oxidation state of a carbon atom in the starting material by either adding an oxygen atom to this carbon or removing an electron from this carbon and as such would be obvious to one of ordinary skill and knowledge in the art. The definition of "oxidant" includes but is not limited to: osmium tetroxide, ruthenium tetroxide, ruthenium trichloride, potassium permanganate, meta-chloroperbenzoic acid, hydrogen peroxide, dimethyl dioxirane and the like.

The term "metal ligand" refers to a molecule that has an unshared pair of electrons and can coordinate to a metal atom and as such would be obvious to one of ordinary skill and knowledge in the art. The definition of "metal ligand" includes but is not limited to: water, alkoxy anion, alkylthio anion, ammonia, trialkylamine, triarylamine, trialkylphosphine, triarylphosphine, cyanide, azide and the like.

The term "reducing reagent" refers to any reagent that will decrease the oxidation state of a carbon atom in the starting material by either adding a hydrogen atom to this carbon or adding an electron to this carbon and as such would be obvious to one of ordinary skill and knowledge in the art. The definition of "reducing reagent" includes but is not limited to: borane-dimethyl sulfide complex, 9-borabicyclo[3.3.1.] nonane (9-BBN), catechol borane, lithium borohydride, sodium borohydride, sodium borohydride-methanol complex, potassium borohydride, sodium hydroxyborohydride, lithium triethylborohydride, lithium n-butylborohydride, sodium cyanoborohydride, calcium (II) borohydride, lithium aluminum hydride, diisobutylaluminum hydride, n-butyl-diisobutylaluminum hydride, sodium bis-methoxyethoxyaluminum hydride, triethoxysilane, diethoxymethylsilane, lithium hydride, lithium, sodium, hydrogen Ni/B, and the like. Certain acidic and Lewis acidic reagents enhance the activity of reducing reagents. Examples of such acidic reagents include: acetic acid, methanesulfonic acid, hydrochloric acid, and the like. Examples of such Lewis acidic reagents include: trimethoxyborane, triethoxyborane, aluminum trichloride, lithium chloride, vanadium trichloride, dicyclopentadienyl titanium dichloride, cesium fluoride, potassium fluoride, zinc (II) chloride, zinc (II) bromide, zinc (II) iodide, and the like.

The term "coupling reagent" refers to any reagent that will activate the carbonyl of a carboxylic acid and facilitate the formation of an ester or amide bond. The definition of "coupling reagent" includes but is not limited to: acetyl chloride, ethyl chloroformate, dicyclohexylcarbodiimide (DCC), diisopropyl carbodiimide (DIC), 1-ethyl-3-(3-dimethylaminopropyl) carbodiimide (EDCI), N-hydroxybenzotriazole (HOBT), N-hydroxysuccinimide (HOSu), 4-nitrophenol, pentafluorophenol, 2-(1H-benzotriazole-1-yl)-1,1,3,3-tetramethyluronium tetrafluoroborate (TBTU), O-benzotriazole-N,N,N'N'-tetramethyluronium hexafluorophosphate (HBTU), benzotriazole-1-yl-oxy-tris-(dimethylamino)-phosphonium hexafluorophosphate (BOP), benzotriazole-1-yl-oxy-tris-pyrrolidinophosphonium hexafluorophosphate, bromo-trispyrrolidino-phosphonium hexafluorophosphate, 2-(5-norbornene-2,3-dicarboximido)-1,1,3,3-tetramethyluronium tetrafluoroborate (TNTU), O—(N-succinimidyl)-1, 1,3,3-tetramethyluronium tetrafluoroborate (TSTU), tetramethylfluoroformamidinium hexafluorophosphate and the like.

The term "removable protecting group" or "protecting group" refers to any group which when bound to a functionality, such as the oxygen atom of a hydroxyl or carboxyl group or the nitrogen atom of an amino group, prevents reactions from occurring at these functional groups and which protecting group can be removed by conventional chemical or enzymatic steps to reestablish the functional group. The particular removable protecting group employed is not critical.

The definition of "hydroxyl protecting group" includes but is not limited to:

Methyl, tert-butyl, allyl, propargyl, p-chlorophenyl, p-methoxyphenyl, p-nitrophenyl, 2,4-dinitrophenyl, 2,3,5,6-tetrafluoro-4-(trifluoromethyl)phenyl, methoxymethyl, methylthiomethyl, (phenyldimethylsilyl)methoxymethyl, benzyloxymethyl, p-methoxy-benzyloxymethyl, p-nitrobenzyloxymethyl, o-nitrobenzyloxymethyl, (4-methoxyphenoxy)methyl, guaiacolmethyl, tert-butoxymethyl, 4-pentenyloxymethyl, tert-butyldimethylsiloxymethyl, thexyldimethylsiloxymethyl, tert-butyldiphenylsiloxymethyl, 2-methoxyethoxymethyl, 2,2,2-trichloroethoxymethyl, bis(2-chloroethoxy)methyl, 2-(trimethylsilyl) ethoxymethyl, menthoxymethyl, 1-ethoxyethyl, 1-(2-chloroethoxy)ethyl, 1-[2-(trimethylsilyl)ethoxy]ethyl, 1-methyl-1-ethoxyethyl, 1-methyl-1-benzyloxyethyl, 1-methyl-1-benzyloxy-2-fluoroethyl, 1-methyl-1-phenoxyethyl, 2,2,2-trichloroethyl, 1-dianisyl-2,2,2-trichloroethyl, 1,1,1,3, 3,3-hexafluoro-2-phenylisopropyl, 2-trimethylsilylethyl, 2-(benzylthio)ethyl, 2-(phenylselenyl)ethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydropyranyl S,S-dioxide, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothiofuranyl and the like;

Benzyl, 2-nitrobenzyl, 2-trifluoromethylbenzyl, 4-methoxybenzyl, 4-nitrobenzyl, 4-chlorobenzyl, 4-bromobenzyl, 4-cyanobenzyl, 4-phenylbenzyl, 4-acylaminobenzyl, 4-azidobenzyl, 4-(methylsulfinyl)benzyl, 2,4-dimethoxybenzyl, 4-azido-3-chlorobenzyl, 3,4-dimethoxybenzyl, 2,6-dichlorobenzyl, 2,6-difluorobenzyl, 1-pyrenylmethyl, diphenylmethyl, 4,4'-dinitrobenzhydryl, 5-benzosuberyl, triphenylmethyl (Trityl), α-naphthyldiphenylmethyl, (4-Methoxyphenyl)-diphenyl-methyl, di-(p-methoxyphenyl)-phenylmethyl, tri-(p-methoxyphenyl)methyl, 4-(4'-bromophenacyloxy)-phenyldiphenylmethyl, 4,4',4"-tris(4,5-dichlorophthalimidophenyl)methyl, 4,4',4"-tris (levulinoyloxyphenyl)methyl, 4,4'-dimethoxy-3"-[N-(imidazolylmethyl)]trityl, 4,4'-dimethoxy-3"-[N-(imidazolylethyl)carbamoyl]trityl, 1,1-bis(4-methoxyphenyl)-1'-pyrenylmethyl, 4-(17-tetrabenzo[a,c,g,I] fluorenylmethyl)-4,4'-dimethoxytrityl, 9-anthryl, 9-(9-phenyl)xanthenyl, 9-(9-phenyl-10-oxo)anthryl and the like;

Trimethylsilyl, triethylsilyl, triisopropylsilyl, dimethylisopropylsilyl, diethylisopropylsilyl, dimethylhexylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenylsilyl, tert-butoxydiphenylsilyl and the like;

—$C(O)R_{20}$, where $R_{20}$ is selected from alkyl, substituted alkyl, aryl and more specifically $R_{20}$=hydrogen, methyl, ethyl, tert-butyl, adamantyl, crotyl, chloromethyl, dichloromethyl, trichloromethyl, trifluoromethyl, methoxymethyl, triphenylmethoxymethyl, phenoxymethyl, 4-chlorophenoxymethyl, phenylmethyl, diphenylmethyl, 4-methoxycrotyl, 3-phenylpropyl, 4-pentenyl, 4-oxopentyl, 4,4-(ethylenedithio)pentyl, 5-[3-bis(4-methoxyphenyl)hydroxymethylphenoxy]-4-oxopentyl, phenyl, 4-methylphenyl, 4-nitrophenyl, 4-fluorophenyl, 4-chlorophenyl, 4-methoxyphenyl, 4-phenylphenyl, 2,4,6-trimethylphenyl, α-naphthyl, benzoyl and the like;

—$C(O)OR_{20}$, where $R_{20}$ is selected from alkyl, substituted alkyl, aryl and more specifically $R_{20}$=methyl, methoxymethyl, 9-fluorenylmethyl, ethyl, 2,2,2-trichloromethyl, 1,1-dimethyl-2,2,2-trichloroethyl, 2-(trimethylsilyl)ethyl, 2-(phenylsulfonyl)ethyl, isobutyl, tert-Butyl, vinyl, allyl, 4-nitrophenyl, benzyl, 2-nitrobenzyl, 4-nitrobenzyl, 4-methoxybenzyl, 2,4-dimethoxybenzyl, 3,4-dimethoxybenzyl, 2-(methylthiomethoxy)ethyl, 2-dansenylethyl, 2-(4-nitrophenyl)ethyl, 2-(2,4-dinitrophenyl)ethyl, 2-cyano-1-phenylethyl, thiobenzyl, 4-ethoxy-1-naphthyl and the like.

The definition of "amino protecting group" includes but is not limited to:

2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 1-methyl-1-(triphenylphosphonio)ethyl, 1,1-dimethyl-2-cyanoethyl, 2-dansylethyl, 2-(4-nitrophenyl)ethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoromethyl)-6-chromonylmethyl, m-nitrophenyl, 3,5-dimethoxybenzyl, 1-methyl-1-(3,5-dimethoxyphenyl)ethyl, o-nitrobenzyl, α-methylnitropiperonyl, 3,4-dimethoxy-6-nitrobenzyl, N-benzenesulfenyl, N-o-nitrobenzenesulfenyl, N-2,4-dinitrobenzenesulfenyl, N-pentachlorobenzenesulfenyl. N-2-nitro-4-methoxybenzenesulfenyl, N-triphenylmethylsulfenyl, N-1-(2,2,2-trifluoro-1,1-diphenyl)ethylsulfenyl, N-3-nitro-2-pyridinesulfenyl, N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6-tetramethyl-4-methoxybenzenesulfonyl and the like;

—$C(O)OR_{20}$, where $R_{20}$ is selected from alkyl, substituted alkyl, aryl and more specifically $R_{20}$=methyl, ethyl, 9-fluorenylmethyl, 9-(2-sulfo)fluorenylmethyl. 9-(2,7-dibromo) fluorenylmethyl, 17-tetrabenzo[a,c,g,i]fluorenylmethyl. 2-chloro-3-indenylmethyl, benz[f]inden-3-ylmethyl, 2,7-di-t-butyl-[9-(10,10-dioxo-10,10,10,10-tetrahydrothloxanthyl)]methyl, 1,1-dioxobenzo[b]thiophene-2-ylmethyl, 2,2,2-trichloroethyl, 2-trimethylsilylethyl, 2-phenylethyl, 1-(1 adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-tert-butylphenyl)-1-methylethyl, 2-(2'-pyridyl)ethyl, 2-(4'-pyridyl)ethyl, 2,2-bis(4'-nitrophenyl)ethyl, N-(2-pivaloylamino)-1,1-dimethylethyl, 2-[(2-nitrophenyl)dithio]-1-phenylethyl, tert-butyl, 1-adamantyl, 2-adamantyl, Vinyl, allyl, 1-isopropylallyl, cinnamyl. 4-nitrocinnamyl, 3-(3'-pyridyl)prop-2-enyl, 8-quinolyl, N-Hydroxypiperidinyl, alkyldithio, benzyl, p-methoxybenzyl, p-nitrobenzyl, p-bromobenzyl. p-chlorobenzyl, 2,4-dichlorobenzyl, 4-methylsulfinylbenzyl, 9-anthrylmethyl, diphenylmethyl, tert-amyl, S-benzyl thiocarbamate, butynyl, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N'-dimethylcarboxamido)benzyl, 1,1-dimethyl-3-(N,N'-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(p-phenylazophenyl)ethyl, 1-methyl-1-phenylethyl, 1-methyl-1-4'-pyridylethyl, phenyl, p-(phenylazo)benzyl, 2,4,6-trimethylphenyl, 4-(trimethylammonium)benzyl, 2,4,6-trimethylbenzyl and the like.

The definition of "carboxyl protecting group" includes but is not limited to:

2-N-(morpholino)ethyl, choline, methyl, methoxyethyl, 9-Fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, pivaloyloxymethyl, phenylacetoxymethyl, triisopropylsilylmethyl, cyanomethyl, acetol, p-bromophenacyl. α-methylphenacyl, p-methoxyphenacyl, desyl, carboxamidomethyl, p-azobenzenecarboxamido-methyl, N-phthalimidomethyl, (methoxyethoxy)ethyl, 2,2,2-trichloroethyl, 2-fluoroethyl, 2-chloroethyl, 2-bromoethyl, 2-iodoethyl, 4-chlorobutyl, 5-chloropentyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl, 2-cyanoethyl, heptyl, tert-butyl, 3-methyl-3-pentyl, dicyclopropylmethyl, 2,4-dimethyl-3-pentyl, cyclopentyl, cyclohexyl, allyl, methallyl, 2-methylbut-3-en-2-yl, 3-methylbut-2-(prenyl), 3-buten-1-yl, 4-(trimethylsilyl)-2-buten-1-yl, cinnamyl, α-methylcinnamyl, propargyl, phenyl, 2,6-dimethylphenyl, 2,6-diisopropylphenyl, 2,6-di-tert-butyl-4-methylphenyl, 2,6-di-tert-butyl-4-methoxyphenyl, p-(methylthio)phenyl, pentafluorophenyl, benzyl, triphenylmethyl, diphenylmethyl, bis(o-nitrophenyl)methyl, 9-anthrylmethyl, 2-(9,10-dioxo)anthrylmethyl. 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-Sulfobenzyl, 4-azidomethoxybenzyl, 4-{a/-[1-(4,4-dimethyl-2,6-dioxocyclohexylidene)-3-methylbutyl]amino}benzyl, piperonyl, 4-picolyl, trimethylsilyl, triethylsilyl, tert-butyldimethylsilyl, isopropyldimethylsilyl, phenyldimethylsilyl, di-tert-butylmethylsilyl, triisopropylsilyl and the like.

The term "Amino acid" refers to any of the naturally occurring amino acids, as well as synthetic analogs and derivatives thereof. Alpha-Amino acids comprise a carbon atom to which is bonded an amino group, a carboxy group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine), substituted arylalkyl (e.g., as in tyrosine), heteroarylalkyl (e.g., as in tryptophan, histidine) and the like.

One of skill in the art will appreciate that the term "amino acid" can also include beta-, gamma-, delta-, omega-amino acids, and the like. Unnatural amino acids are also known in the art, as set forth in, Natchus, M. G. Organic Synthesis: Theory and Applications (2001), 5, 89-196; Ager, D. J. Current Opinion in Drug Discovery & Development (2001), 4(6), 800; Reginato, G. Recent Research Developments in Organic Chemistry (2000), 4(Pt. 1), 351-359; Dougherty, D. A. Current Opinion in Chemical Biology (2000), 4(6), 645-652; Lesley, S. A. Drugs and the Pharmaceutical Sciences (2000), 101 (Peptide and Protein Drug Analysis), 191-205; Pojitkov, A. E. Journal of Molecular Catalysis B: Enzymatic (2000), 10(1-3), 47-55; Ager, D. J. Speciality Chemicals (1999), 19(1), 10-12, and all references cited therein. Stereoisomers (e.g., D-amino acids) of the twenty conventional amino acids, unnatural amino acids such as alpha, alpha-disubstituted amino acids and other unconventional amino acids may also be suitable components for compounds of the present invention. Examples of unconventional amino acids include: 4-hydroxyproline, 3-methylhistidine, 5-hydroxylysine, and other similar amino acids and imino acids (e.g., 4-hydroxyproline).

The term "N-protected amino acid" refers to any amino acid which has a protecting group bound to the nitrogen of the amino functionality. This protecting group prevents reactions from occurring at the amino functional group and can be removed by conventional chemical or enzymatic steps to reestablish the amino functional group. The particular protecting group employed is not critical.

The term "O-protected amino acid" refers to any amino acid which has a protecting group bound to the oxygen of the carboxyl functionality. This protecting group prevents reactions from occurring at the carboxyl functional group and can be removed by conventional chemical or enzymatic steps to reestablish the carboxyl functional group. The particular protecting group employed is not critical.

The term "Prodrug" refers to an agent that is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A prodrug may be converted into the parent drug by various mechanisms, including enzymatic processes and metabolic hydrolysis. See Harper, "Drug Latentiation" in Jucker, ed. Progress in Drug Research 4:221-294 (1962); Morozowich et al., "Application of Physical Organic Principles to Prodrug Design" in E. B. Roche ed. Design of Biopharmaceutical Properties through Prodrugs and Analogs, APHA Acad. Pharm. Sci. (1977); Bioreversible Carriers in Drug in Drug Design, Theory and Application, E. B. Roche, ed., APHA Acad. Pharm. Sci. (1987); Design of Prodrugs, H. Bundgaard, Elsevier (1985); Wang et al. "Prodrug approaches to the improved delivery of peptide drug" in Curr. Pharm. Design. 5(4):265-287 (1999); Pauletti et al. (1997) Improvement in peptide bioavailability: Peptidomimetics and Prodrug Strategies, Adv. Drug. Delivery Rev. 27:235-256; Mizen et al. (1998) "The Use of Esters as Prodrugs for Oral Delivery of .beta.-Lactam antibiotics," Pharm. Biotech. 11:345-365; Gaignault et al. (1996) "Designing Prodrugs and Bioprecursors I. Carrier Prodrugs," Pract. Med. Chem. 671-696; Asgharnejad, "Improving Oral Drug Transport", in Transport Processes in Pharmaceutical Systems, G. L. Amidon, P. I. Lee and E. M. Topp, Eds., Marcell Dekker, p. 185-218 (2000); Balant et al., "Prodrugs for the improvement of drug absorption via different routes of administration", Eur. J. Drug Metab. Pharmacokinet., 15(2): 143-53 (1990); Balimane and Sinko, "Involvement of multiple transporters in the oral absorption of nucleoside analogues", Adv. Drug Delivery Rev., 39(1-3): 183-209 (1999); Browne, "Fosphenyloin (Cerebyx)", Clin. Neuropharmacol. 20(1): 1-12 (1997); Bundgaard, "Bioreversible derivatization of drugs—principle and applicability to improve the therapeutic effects of drugs", Arch. Pharm. Chemi 86(1): 1-39 (1979); Bundgaard H. "Improved drug delivery by the prodrug approach", Controlled Drug Delivery 17: 179-96 (1987); Bundgaard H. "Prodrugs as a means to improve the delivery of peptide drugs", Adv. Drug Delivery Rev. 8(1): 1-38 (1992); Fleisher et al. "Improved oral drug delivery: solubility limitations overcome by the use of prodrugs", Adv. Drug Delivery Rev. 19(2): 115-130 (1996); Fleisher et al. "Design of prodrugs for improved gastrointestinal absorption by intestinal enzyme targeting", Methods Enzymol. 112 (Drug Enzyme Targeting, Pt. A): 360-81, (1985); Farquhar D, et al., "Biologically Reversible Phosphate-Protective Groups", J. Pharm. Sci., 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," J. Chem. Soc., Chem. Commun., 875-877 (1991); Friis and Bundgaard, "Prodrugs of phosphates and phosphonates: Novel lipophilic alpha-acyloxyalkyl ester derivatives of phosphate- or phosphonate containing drugs masking the negative charges of these groups", Eur. J. Pharm. Sci. 4: 49-59 (1996); Gangwar et al., "Pro-drug, molecular structure and percutaneous delivery", Des. Biopharm. Prop. Prodrugs Analogs, [Symp.] Meeting Date 1976, 409-21. (1977); Nathwani and Wood, "Penicillins: a current review of their clinical pharmacology and therapeutic use", Drugs 45(6): 866-94 (1993); Sinhababu and Thakker, "Prodrugs of anticancer agents", Adv. Drug Delivery Rev. 19(2): 241-273 (1996); Stella et al., "Prodrugs. Do they have advantages in clinical practice?", Drugs 29(5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1-3): 117-151 (1999); Taylor, "Improved passive oral drug delivery via prodrugs", Adv. Drug Delivery Rev., 19(2): 131-148 (1996); Valentino and Borchardt, "Prodrug strategies to enhance the intestinal absorption of peptides", Drug Discovery Today 2(4): 148-155 (1997); Wiebe and Knaus, "Concepts for the design of anti-HIV nucleoside prodrugs for treating cephalic HIV infection", Adv. Drug Delivery Rev.: 39(1-3):63-80 (1999); Waller et al., "Prodrugs", Br. J. Clin. Pharmac. 28: 497-507 (1989).

The terms "halogen", "halide" or "halo" include fluorine, chlorine, bromine, and iodine.

The terms "alkyl" and "substituted alkyl" are interchangeable and include substituted and unsubstituted $C_1$-$C_{10}$ straight chain saturated aliphatic hydrocarbon groups, substituted and unsubstituted $C_2$-$C_{10}$ straight chain unsaturated aliphatic hydrocarbon groups, substituted and unsubstituted $C_4$-$C_{10}$ branched saturated aliphatic hydrocarbon groups, substituted and unsubstituted $C_4$-$C_{10}$ branched unsaturated aliphatic hydrocarbon groups, substituted and unsubstituted $C_3$-$C_8$ cyclic saturated aliphatic hydrocarbon groups, substituted and unsubstituted $C_5$-$C_8$ cyclic unsaturated aliphatic hydrocarbon groups having the specified number of carbon atoms. For example, the definition of "alkyl" shall include but is not limited to: methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like. Alkyl substituents are independently selected from a group consisting of halogen, —OH, —SH, —NH$_2$, —CN, —NO$_2$, =O, =CH$_2$, trihalomethyl, carbamoyl, arylC$_{0-10}$alkyl, heteroarylC$_{0-10}$alkyl, C$_{1-10}$alkyloxy, arylC$_{0-10}$alkyloxy, C$_{1-10}$alkylthio, arylC$_{0-10}$alkylthio, C$_{1-10}$alkylamino, arylC$_{0-10}$alkylamino, N-aryl-N—C$_{0-10}$alkylamino, C$_{1-10}$alkylcarbonyl, arylC$_{0-10}$alkylcarbonyl, C$_{1-10}$alkylcarboxy, aryl C$_{0-10}$alkylcarboxy, C$_{1-10}$alkylcarbonylamino, arylC$_{0-10}$alkylcarbonylamino, tetrahydrofuryl, morpholinyl, piperazinyl, hydroxypyronyl, —C$_{0-10}$alkylCOOR$_{21}$ and —C$_{0-10}$alkylCONR$_{22}$R$_{23}$ wherein R$_{21}$, R$_{22}$ and R$_{23}$ are independently selected from hydrogen, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined herein.

The term "alkyloxy" (e.g. methoxy, ethoxy, propyloxy, allyloxy, cyclohexyloxy) represents a substituted or unsubstituted alkyl group as defined above having the indicated number of carbon atoms attached through an oxygen bridge. The term "alkyloxyalkyl" represents an alkyloxy group attached through an alkyl or substituted alkyl group as defined above having the indicated number of carbon atoms.

The term "alkylthio" (e.g. methylthio, ethylthio, propylthio, cyclohexenylthio and the like) represents a substituted or unsubstituted alkyl group as defined above having the indicated number of carbon atoms attached through a sulfur bridge. The term "alkylthioalkyl" represents an alkylthio group attached through an alkyl or substituted alkyl group as defined above having the indicated number of carbon atoms.

The term "alkylamino" (e.g. methylamino, diethylamino, butylamino, N-propyl-N-hexylamino, (2-cyclopentyl)propylamino, hexenylamino, and the like) represents one or two substituted or unsubstituted alkyl groups as defined above having the indicated number of carbon atoms attached through an amine bridge. The substituted or unsubstituted alkyl groups maybe taken together with the nitrogen to which they are attached forming a saturated cyclic or unsaturated cyclic system containing 3 to 10 carbon atoms with at least one substituent as defined above. The term "alkylaminoalkyl" represents an alkylamino group attached through a substituted or unsubstituted alkyl group as defined above having the indicated number of carbon atoms.

The term "alkylhydrazino" (e.g. methylhydrazino, diethylhydrazino, butylhydrazino, (2-cyclopentyl)propylhydrazino, cyclohexanehydrazino, and the like) represents one or two substituted or unsubstituted alkyl groups as defined above having the indicated number of carbon atoms attached through a nitrogen atom of a hydrazine bridge. The substituted or unsubstituted alkyl groups maybe taken together with the nitrogen to which they are attached forming a saturated cyclic or unsaturated cyclic system containing 3 to 10 carbon atoms with at least one substituent as defined above. The term "alkylhydrazinoalkyl" represents an alkylhydrazino group attached through a substituted or unsubstituted alkyl group as defined above having the indicated number of carbon atoms.

The term "alkylcarbonyl" (e.g. cyclooctylcarbonyl, pentylcarbonyl, 3-hexenylcarbonyl and the like) represents a substituted or unsubstituted alkyl group as defined above having the indicated number of carbon atoms attached through a carbonyl group. The term "alkylcarbonylalkyl" represents an alkylcarbonyl group attached through a substituted or unsubstituted alkyl group as defined above having the indicated number of carbon atoms.

The term "alkylcarboxy" (e.g. heptylcarboxy, cyclopropylcarboxy, 3-pentenylcarboxy and the like) represents an alkylcarbonyl group as defined above wherein the carbonyl is in turn attached through an oxygen. The term "alkylcarboxyalkyl" represents an alkylcarboxy group attached through an alkyl group as defined above having the indicated number of carbon atoms.

The term "alkylcarbonylamino" (e.g. hexylcarbonylamino, cyclopentylcarbonylaminomethyl, methylcarbonylaminophenyl and the like) represents an alkylcarbonyl group as defined above wherein the carbonyl is in turn attached through the nitrogen atom of an amino group. The nitrogen group may itself be substituted with a substituted or unsubstituted alkyl or aryl group. The term "alkylcarbonylaminoalkyl" represents an alkylcarbonylamino group attached through a substituted or unsubstituted alkyl group as defined above having the indicated number of carbon atoms.

The term "alkylcarbonylhydrazino" (e.g. ethylcarbonylhydrazino, tert-butylcarbonylhydrazino and the like) represents an alkylcarbonyl group as defined above wherein the carbonyl is in turn attached through the nitrogen atom of a hydrazino group.

The term "aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from a group consisting of halogen, —OH, —SH, —CN, —NO$_2$, trihalomethyl, hydroxypyronyl, C$_{1-10}$alkyl, arylC$_{0-10}$alkyl, C$_{0-10}$alkyloxyC$_{0-10}$alkyl, aryl C$_{0-10}$alkyloxyC$_{0-10}$alkyl, C$_{0-10}$alkylthioC$_{0-10}$alkyl, arylC$_{0-10}$alkylthioC$_{0-10}$alkyl, C$_{0-10}$alkylaminoC$_{0-10}$alkyl, arylC$_{0-10}$alkylaminoC$_{0-10}$alkyl, N-aryl-N—C$_{0-10}$alkylaminoC$_{0-10}$alkyl, C$_{0-10}$alkylcarbonylC$_{0-10}$alkyl, arylC$_{0-10}$alkylcarbonylC$_{0-10}$alkyl, C$_{1-10}$alkylcarboxyC$_{0-10}$alkyl, arylC$_{0-10}$alkylcarboxyC$_{0-10}$alkyl, C$_{1-10}$alkylcarbonylaminoC$_{0-10}$alkyl, aryl C$_{0-10}$alkylcarbonylaminoC$_{0-10}$alkyl, —C$_{0-10}$alkylCOOR$_{21}$, and —C$_{0-10}$alkylCONR$_{22}$R$_{23}$ wherein R$_{21}$, R$_{22}$ and R$_{23}$ are independently selected from hydrogen, alkyl, aryl or R$_{22}$ and R$_{23}$ are taken together with the nitrogen to which they are attached forming a saturated cyclic or unsaturated cyclic system containing 3 to 8 carbon atoms with at least one substituent as defined above.

The definition of "aryl" includes but is not limited to phenyl, biphenyl, naphthyl, dihydronaphthyl, tetrahydronaphthyl, indenyl, indanyl, azulenyl, anthryl, phenanthryl, fluorenyl, pyrenyl and the like.

The term "arylalkyl" (e.g. (4-hydroxyphenyl)ethyl, (2-aminonaphthyl)hexenyl and the like) represents an aryl group as defined above attached through a substituted or unsubstituted alkyl group as defined above having the indicated number of carbon atoms.

The term "arylcarbonyl" (e.g. 2-thiophenylcarbonyl, 3-methoxyanthrylcarbonyl and the like) represents an aryl group as defined above attached through a carbonyl group.

The term "arylalkylcarbonyl" (e.g. (2,3-dimethoxyphenyl) propylcarbonyl, (2-chloronaphthyl)pentenyl-carbonyl and the like) represents an arylalkyl group as defined above wherein the alkyl group is in turn attached through a carbonyl.

The term "aryloxy" (e.g. phenoxy, naphthoxy, 3-methylphenoxy, and the like) represents an aryl or substituted aryl group as defined above having the indicated number of carbon atoms attached through an oxygen bridge. The term "aryloxyalkyl" represents an aryloxy group attached through a substituted or unsubstituted alkyl group as defined above having the indicated number of carbon atoms.

The term "arylthio" (e.g. phenylthio, naphthylthio, 3-bromophenylthio, and the like) represents an aryl or substituted aryl group as defined above having the indicated number of carbon atoms attached through a sulfur bridge. The term "arylthioalkyl" represents an arylthio group attached through a substituted or unsubstituted alkyl group as defined above having the indicated number of carbon atoms.

The term "arylamino" (e.g. phenylamino, diphenylamino, naphthylamino, N-phenyl-N-naphthylamino, o-methylphenylamino, p-methoxyphenylamino, and the like) represents one or two aryl groups as defined above having the indicated number of carbon atoms attached through an amine bridge. The term "arylaminoalkyl" represents an arylamino group attached through a substituted or unsubstituted alkyl group as defined above having the indicated number of carbon atoms. The term "arylalkylamino" represents an aryl group attached through an alkylamino group as defined above having the indicated number of carbon atoms. The term "N-aryl-N-alkylamino" (e.g. N-phenyl-N-methylamino, N-naphthyl-N-butylamino, and the like) represents one aryl and one a substituted or unsubstituted alkyl group as defined above having the indicated number of carbon atoms independently attached through an amine bridge.

The term "arylhydrazino" (e.g. phenylhydrazino, naphthylhydrazino, 4-methoxyphenylhydrazino, and the like) represents one or two aryl groups as defined above having the indicated number of carbon atoms attached through a hydrazine bridge. The term "arylhydrazinoalkyl" represents an arylhydrazino group attached through a substituted or unsubstituted alkyl group as defined above having the indicated number of carbon atoms. The term "arylalkylhydrazino" represents an aryl group attached through an alkylhydrazino group as defined above having the indicated number of carbon atoms. The term "N-aryl-N-alkylhydrazino" (e.g. N-phenyl-N-methylhydrazino, N-naphthyl-N-butylhydrazino, and the like) represents one aryl and one a substituted or unsubstituted alkyl group as defined above having the indicated number of carbon atoms independently attached through an amine atom of a hydrazine bridge.

The term "arylcarboxy" (e.g. phenylcarboxy, naphthylcarboxy, 3-fluorophenylcarboxy and the like) represents an arylcarbonyl group as defined above wherein the carbonyl is in turn attached through an oxygen bridge. The term "arylcarboxyalkyl" represents an arylcarboxy group attached through a substituted or unsubstituted alkyl group as defined above having the indicated number of carbon atoms.

The term "arylcarbonylamino" (e.g. phenylcarbonylamino, naphthylcarbonylamino, 2-methylphenylcarbonylamino and the like) represents an arylcarbonyl group as defined above wherein the carbonyl is in turn attached through the nitrogen atom of an amino group. The nitrogen group may itself be substituted with an a substituted or unsubstituted alkyl or aryl group. The term "arylcarbonylaminoalkyl" represents an arylcarbonylamino group attached through a substituted or unsubstituted alkyl group as defined above having the indicated number of carbon atoms. The nitrogen group may itself be substituted with a substituted or unsubstituted alkyl or aryl group.

The term "arylcarbonylhydrazino" (e.g. phenylcarbonylhydrazino, naphthylcarbonylhydrazino, and the like) represents an arylcarbonyl group as defined above wherein the carbonyl is in turn attached through the nitrogen atom of a hydrazino group.

The terms "heteroaryl", "heterocycle" or "heterocyclic" refers to a monovalent unsaturated group having a single ring or multiple condensed rings, from 1 to 8 carbon atoms and from 1 to 4 hetero atoms selected from nitrogen, sulfur or oxygen within the ring. The heteroaryl groups in this invention can be optionally substituted with 1 to 3 substituents selected from a group consisting of: halogen, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_{21}$, and —$C_{0-10}$alkylCONR$_{22}$R$_{23}$ wherein R$_{21}$, R$_{22}$ and R$_{23}$ are independently selected from hydrogen, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined above.

The definition of "heteroaryl" includes but is not limited to thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl, 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5]tetrazinanyl-3,6-dione, dihydro-pyrimidinyl-2,4-dione, pyrimidinyl-2,4,6-trione and the like. For the purposes of this application, the terms "heteroaryl", "heterocycle" or "heterocyclic" do not include carbohydrate rings (i.e. mono- or oligosaccharides).

The term "saturated heterocyclic" represents an unsubstituted, mono-, di- or trisubstituted monocyclic, polycyclic saturated heterocyclic group covalently attached at any ring position capable of forming a stable covalent bond, certain preferred points of attachment being apparent to those skilled in the art (e.g., 1-piperidinyl, 4-piperazinyl and the like).

The saturated heterocyclic substituents are independently selected from a group consisting of halo, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_{21}$, and —$C_{0-10}$alkylCONR$_{22}$R$_{23}$ wherein R$_{21}$, R$_{22}$ and R$_{23}$ are independently selected from hydrogen, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined above.

The definition of saturated heterocyclic includes but is not limited to pyrrolidinyl, pyrazolidinyl, piperidinyl, 1,4-dioxanyl, morpholinyl, 1,4-dithienyl, thiomorpholinyl, piperazinyl, quinuclidinyl, and the like.

The term "alpha-beta-unsaturated carbonyl" refers to a molecule that has a carbonyl group directly attached to a double or triple bonded carbon and which would be obvious to one of ordinary skill and knowledge in the art. The definition of alpha-beta-unsaturated carbonyl includes but is not limited to acrolein, methyl vinyl ketone, and the like.

In another embodiment of the invention, there are provided pharmaceutical compositions comprising at least one of the compounds of the invention, as well as pharmaceutically acceptable pro-drugs and salts of such compounds, in a pharmaceutically acceptable vehicle, for enteral, parenteral, topical or ocular administration.

In another embodiment of the invention, there are provided pharmaceutical compositions comprising an effective regulating amount of at least one of the compounds of the invention in combination with a pharmaceutically acceptable carrier, for control of cellular processes, cellular differentiation, cellular proliferation or apoptosis.

In another embodiment of the invention, there are provided pharmaceutical compositions comprising in a pharmaceutically acceptable vehicle suitable for enteral, parenteral, or topical administration, one or more compounds of the invention for treating a mammalian subject wherein said wherein said compound exerts its therapeutic effects via the in vivo modulation of lipid metabolism, lipid homeostasis, hyperlipidemia, skin-related processes, autoimmune diseases, fatty acid metabolism, malignant cell development, premalignant lesions, programmed cell death, endocrinological processes, or AP-1 metabolism.

In another embodiment of the invention, there are provided pharmaceutical compositions comprising at least one of the compounds of the invention, in a pharmaceutically acceptable vehicle, for the treatment of carcinomas. Examples of carcinomas include mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia, and the like.

In another embodiment of the invention, there are provided pharmaceutical compositions comprising at least one the compounds of the invention in combination with other chemotherapeutic agents, in a pharmaceutically acceptable vehicle, for the treatment of carcinomas. Examples of chemotherapeutic agents contemplated for use in the practice of this particular invention include Busulfan, Carboplatin, Cisplatin, Cyclophosphamide, Cytosine arabinoside, Etoposide, 5-Fluorouracil, Melphalan, Methotrexate, Mitoxantrone, Taxol, Interferon, Fareston, Arzoxifene, Evista, Tamoxifen, and the like.

In another embodiment of the invention, there are provided pharmaceutical compositions comprising at least one the compounds of the invention in combination with one or more antiestrogenic agents, in a pharmaceutically acceptable vehicle, for the treatment of mammary carcinoma. Examples of antiestrogenic agents contemplated for use in the practice of this particular invention include Fareston, Arzoxifene, Evista, Tamoxifen, and the like.

In another embodiment of the invention, there are provided cosmeceutical compositions comprising at least one the compounds of the invention, in a cosmetically acceptable vehicle, for dermal indications, acne, and psoriasis.

In another embodiment of the invention, there are provided pharmaceutical compositions comprising at least one the compounds of the invention, in a pharmaceutically acceptable vehicle, for the treatment of diabetes, type I diabetes, type II diabetes, impaired glucose tolerance, insulin resistance, obesity, immune dysfunctions including autoimmunity, diseases with dysfunctions of the coagulation system, allergic diseases, diseases with decreased or increased synthesis or effects of growth hormone, and diseases with decreased or increased synthesis of hormones or cytokines that regulate the release of/or response to growth hormone.

In another embodiment, the present invention provides a process for preparing a compound of formula F. Such a process can be performed, for example, by contacting a compound of formula D with a compound of formula E under conditions suitable to form compound of formula F, as set forth below:

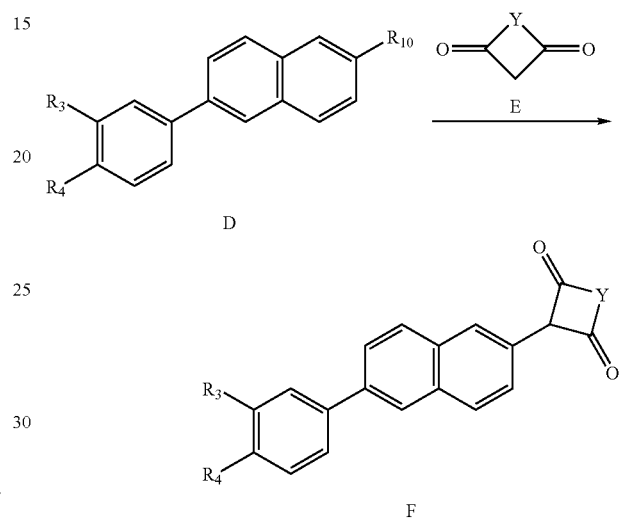

In the scheme shown above, $R_3$, $R_4$ and Y are as defined above, and $R_{10}$ is typically halogen, $-OSO_2R_{11}$ where $R_{11}$ is typically alkyl, substituted alkyl, aryl and substituted aryl Solvents contemplated for use in the practice of this particular invention process can be ethereal solvents, such as for example, diethyl ether, dioxane, tetrahydrofuran, and the like, aromatic solvents, such as for example, toluene, benzene, and the like, and hydroxylic solvents, such as for example, water, methanol, tert-butanol and the like, or any suitable mixtures thereof. The process is typically carried out at a temperature in the range of about 25° C. up to about 120° C.

Compound D can be contacted with compound of formula E in the presence of a mixture of a palladium catalyst, a ligand and a base. Palladium catalysts contemplated for use in the practice of this particular invention process include palladium (II) species such as for example palladium (II) acetate, tris (dibenzylideneacetone)-dipalladium, palladium (II) acetylacetonate, palladium (II) bromide, palladium (II) chloride, palladium (II) hexafluoroacetylacetonate, palladium (II) sulfate, palladium (II) trifluoroacetate and the like. Ligands contemplated for use in the practice of this particular invention process include racemic-2,2'-bis(diphenylphosphino)-1,1'-binaphthyl, (R)-(+)-2,2'-bis(diphenylphosphino)-1,1'-binaphthyl, (S)-(−)-2,2'-bis(diphenylphosphino)-1,1'-binaphthyl, racemic-2,2'-bis(di-p-tolylphosphino)-1,1'-binaphthyl, (R)-(+)-2,2'-bis(di-p-tolylphosphino)-1,1'-binaphthyl, (S)-(−)-2,2'-bis(di-p-tolylphosphino)-1,1'-binaphthyl, racemic-2-(di-tert-butylphosphino)-1,1'-binaphthyl, (R)-2-(di-tert-butylphosphino)-1,1'-binaphthyl, (S)-2-(di-tert-butylphosphino)-1,1'-binaphthyl, 9,9-Dimethyl-4,5-bis(diphenylphosphino)xanthene, 2,2'-bis-(diphenylphosphino)-1,1'-biphenyl, racemic 4,12-bis (diphenylphosphino)-[2.2]-paracyclophane, (R)-(−)-4,12-bis(diphenylphosphino)-[2.2]-paracyclophane, (S)-(+)-4,12-bis(diphenylphosphino)-[2.2]-paracyclophane, 2-(dicyclohexylphosphino)biphenyl, 2-dicyclohexylphosphino-2'-(N,N-dimethylamino)-1,1'-biphenyl, 2-dicyclohexylphosphino-2'-methyl-1,1'-biphenyl, 2-dicyclohexylphosphino-2'-isopropyl-1,1'-biphenyl, (2-dicyclohexylphosphino)-2',4',6'-triisopropyl-1,1'-biphenyl, 2-dicyclohexylphosphino-2',6'-dimethoxy-1,1'-biphenyl, 2-(di-tert-butylphosphino)-1,1'-biphenyl, 2-di-tert-butylphosphino-2'-(N,N-dimethylamino)-1,1'-biphenyl, 2-di-tert-butylphosphino-2'-methylbiphenyl, 2-di-tert-butylphosphino-2'-isopropylbiphenyl, (2-di-tert-butylphosphino)-2',4',6'-triisopropyl biphenyl, (2-di-tert-butylphosphino)-2',6'-dimethoxybiphenyl, 2-(diphenylphosphino)biphenyl, 2-(diphenylphosphino)-2'-(N,N-dimethylamino)biphenyl, 2-diphenylphosphino-2'-methylbiphenyl, 2-diphenylphosphino-2'-isopropylbiphenyl, (2-diphenylphosphino)-2',4',6'-triisopropyl biphenyl, (2-diphenylphosphino)-2',6'-dimethoxybiphenyl, 1,1-bis-(di-tert-butylphosphino)ferrocene, 1-diphenylphosphino-2-(di-tert-butylphosphino)-ethylferrocene, tri-tert-butylphosphine, tricyclohexylphosphine, and the like. Bases contemplated for use in the practice of this particular invention process include sodium tert-butoxide, potassium tert-butoxide, cesium carbonate, potassium carbonate, potassium phosphate tribasic ($K_3PO_4$), and the like.

Invention compounds include

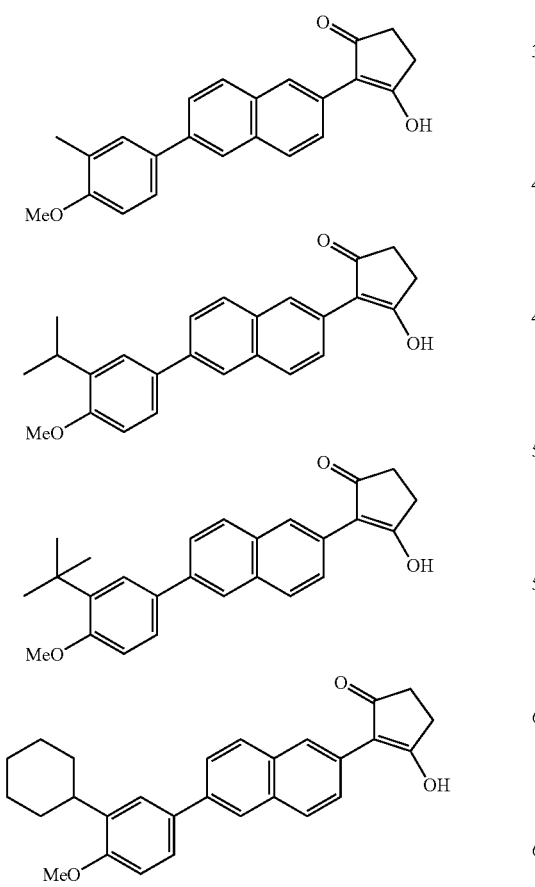

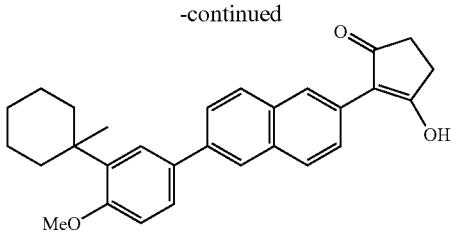

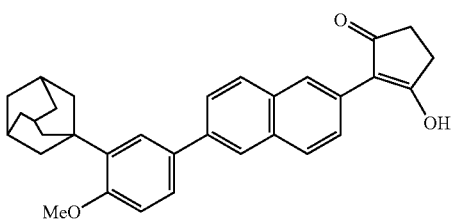

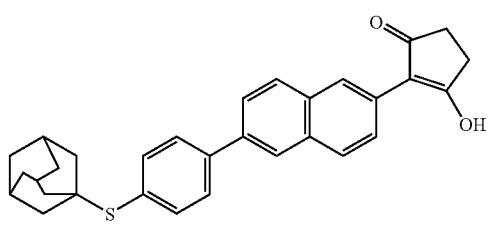

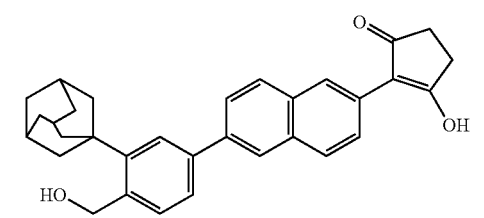

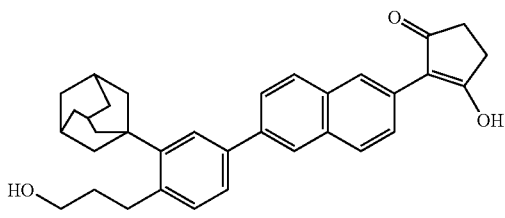

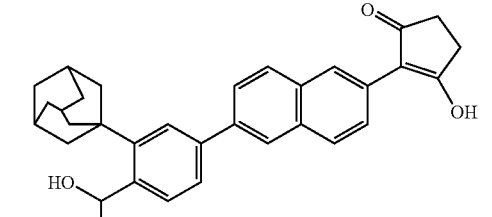

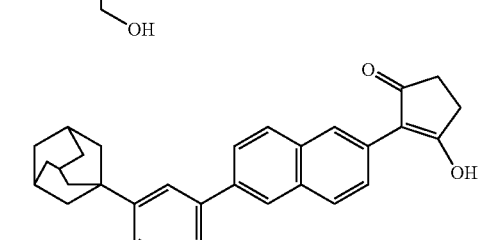

-continued
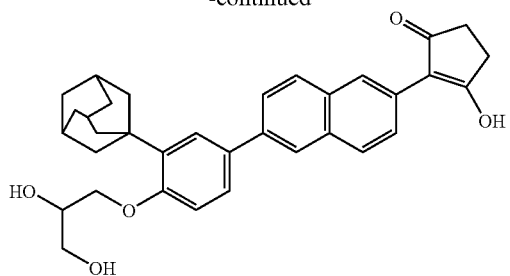
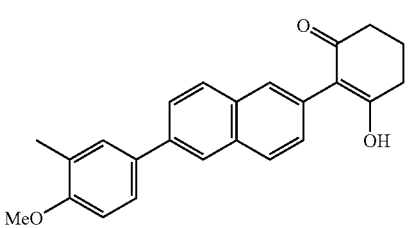
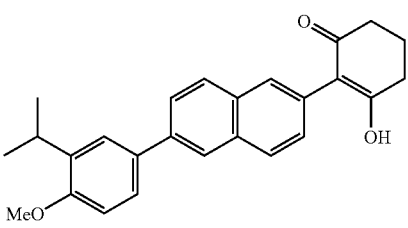
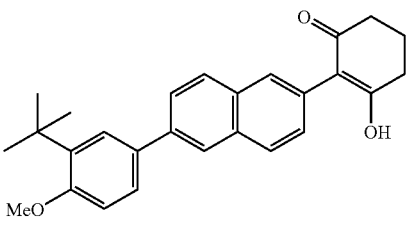
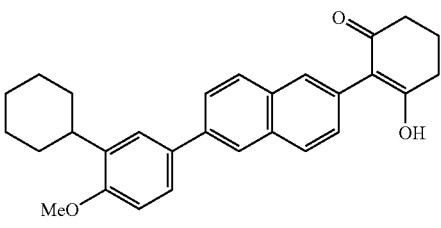
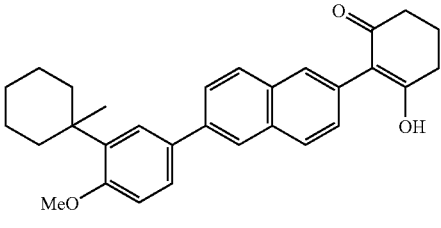
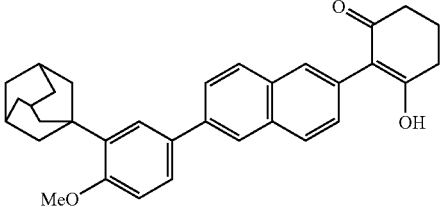
-continued
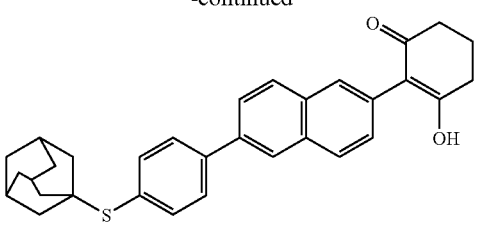
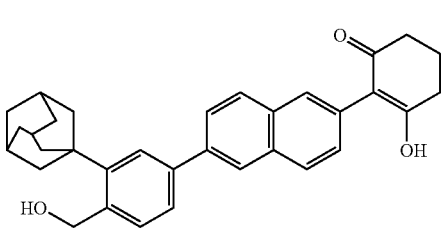
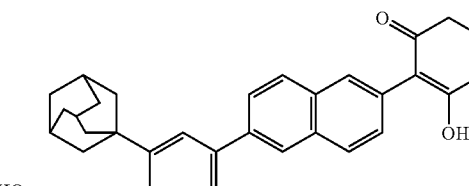
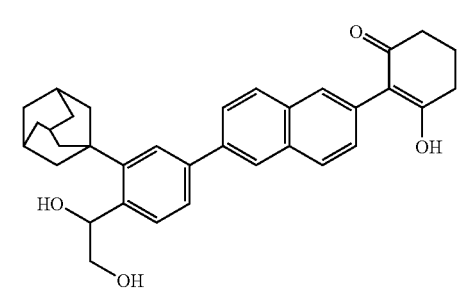
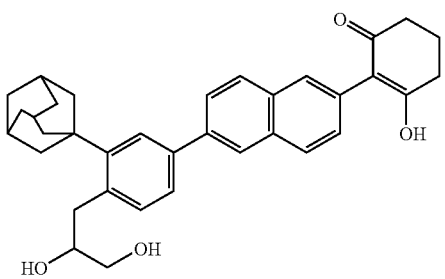
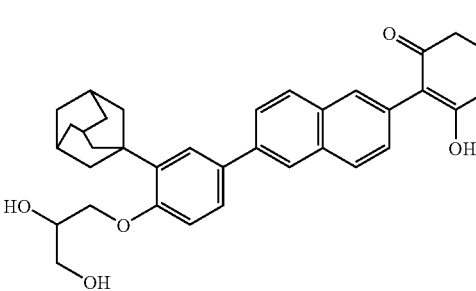

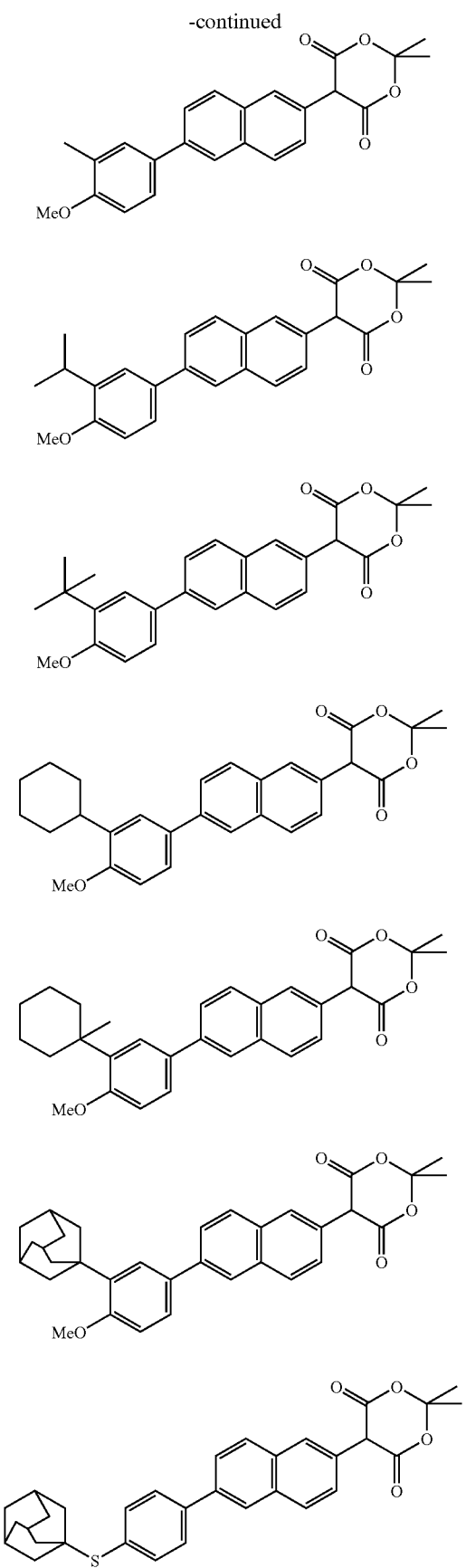
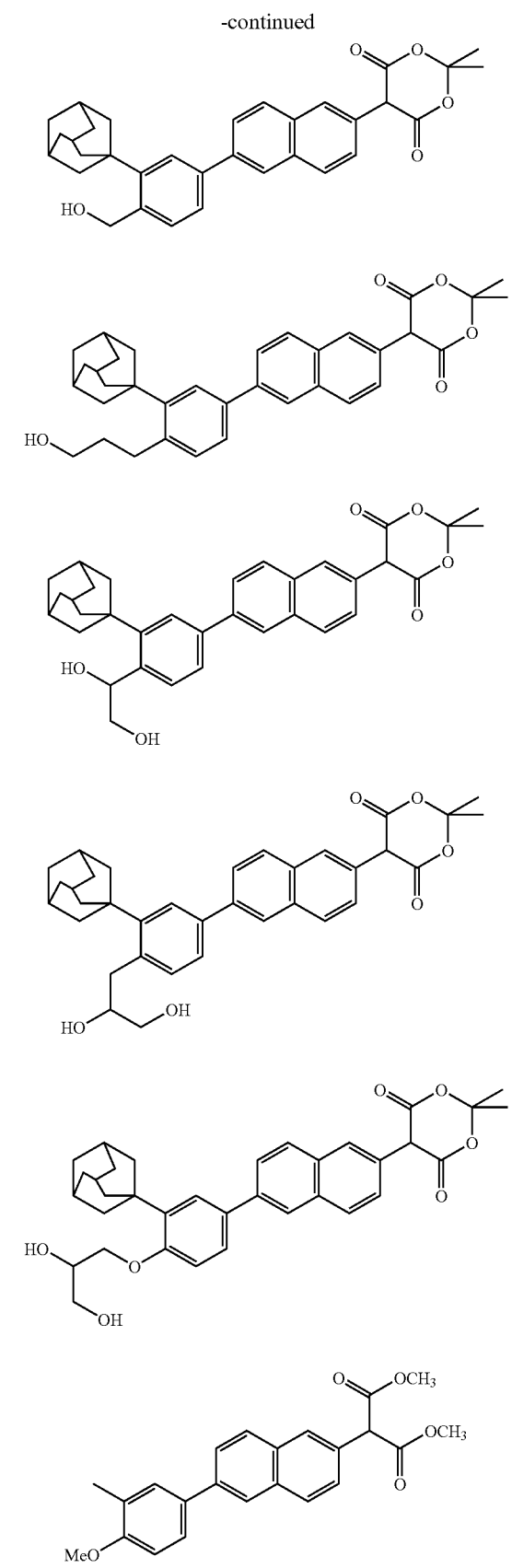

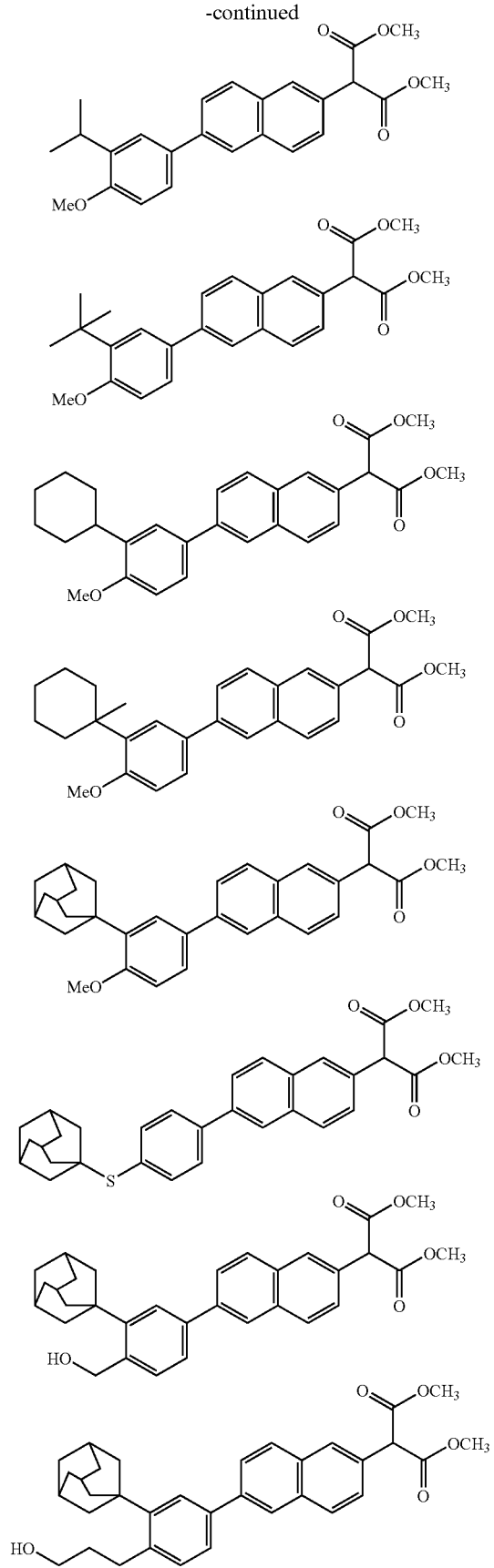
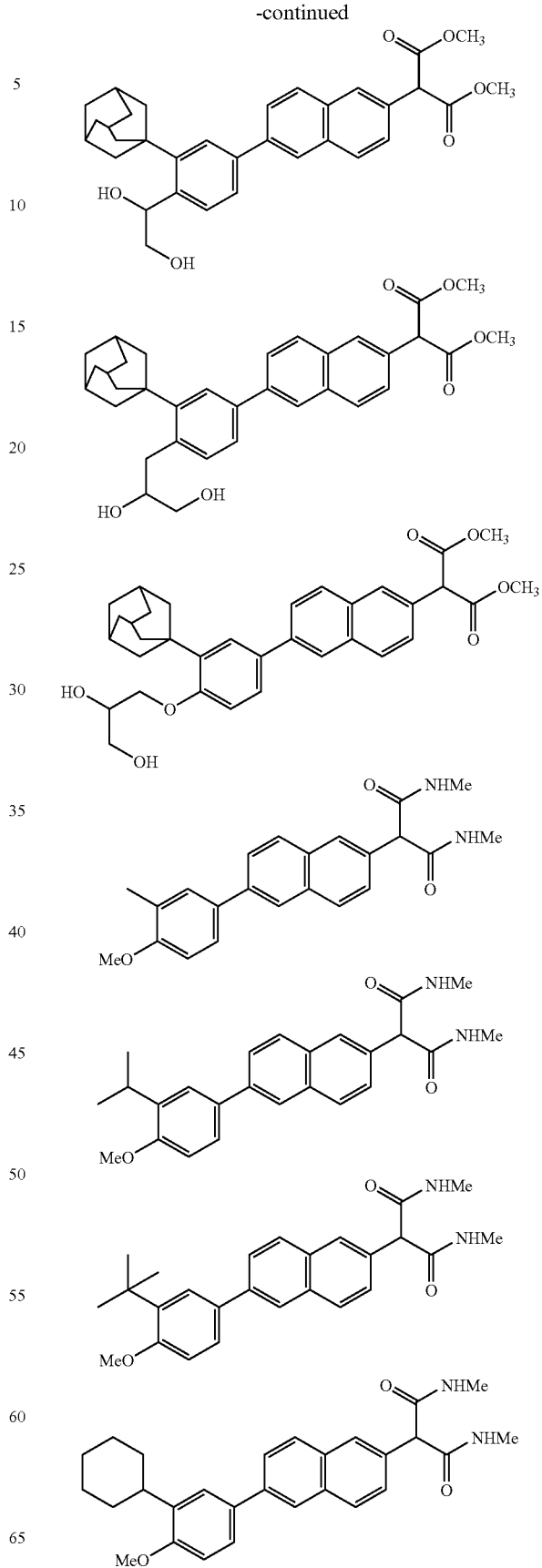

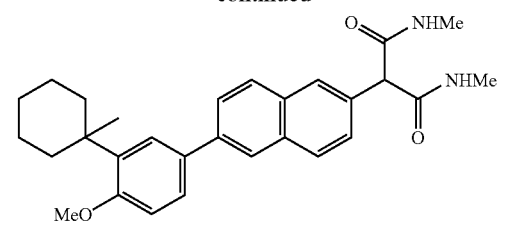
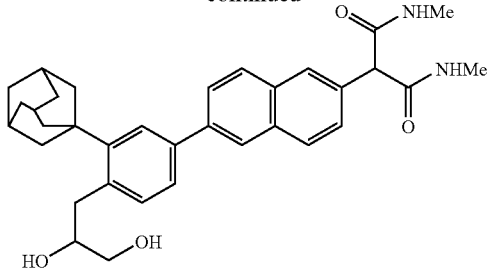
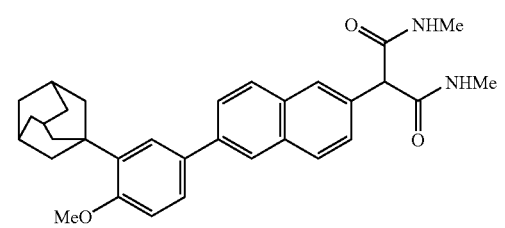
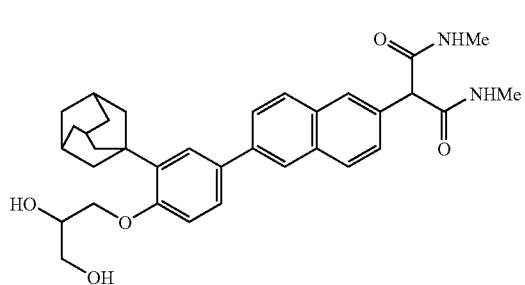
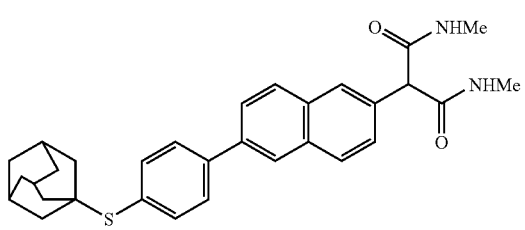
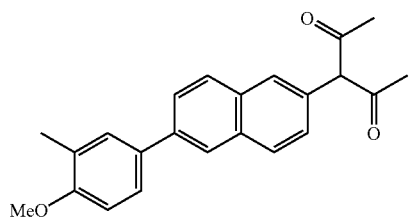
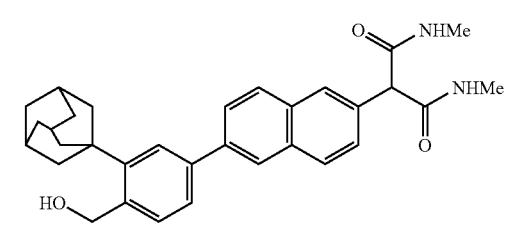
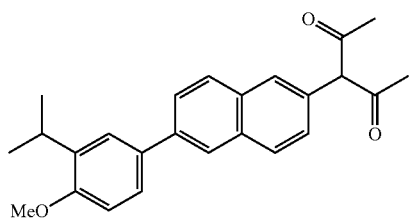
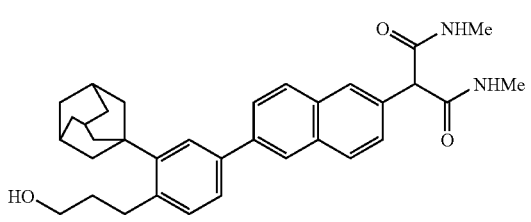
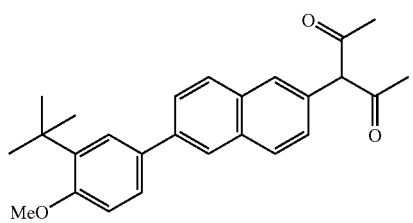
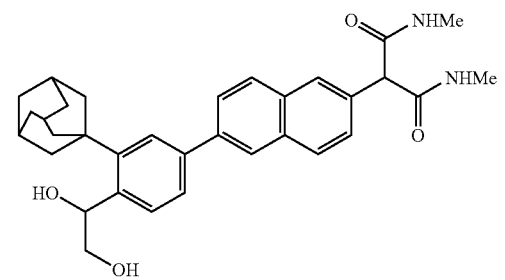
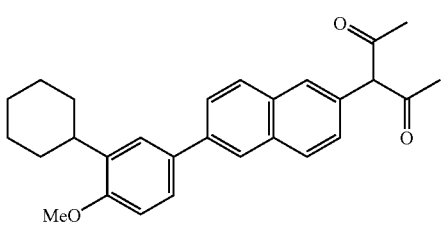

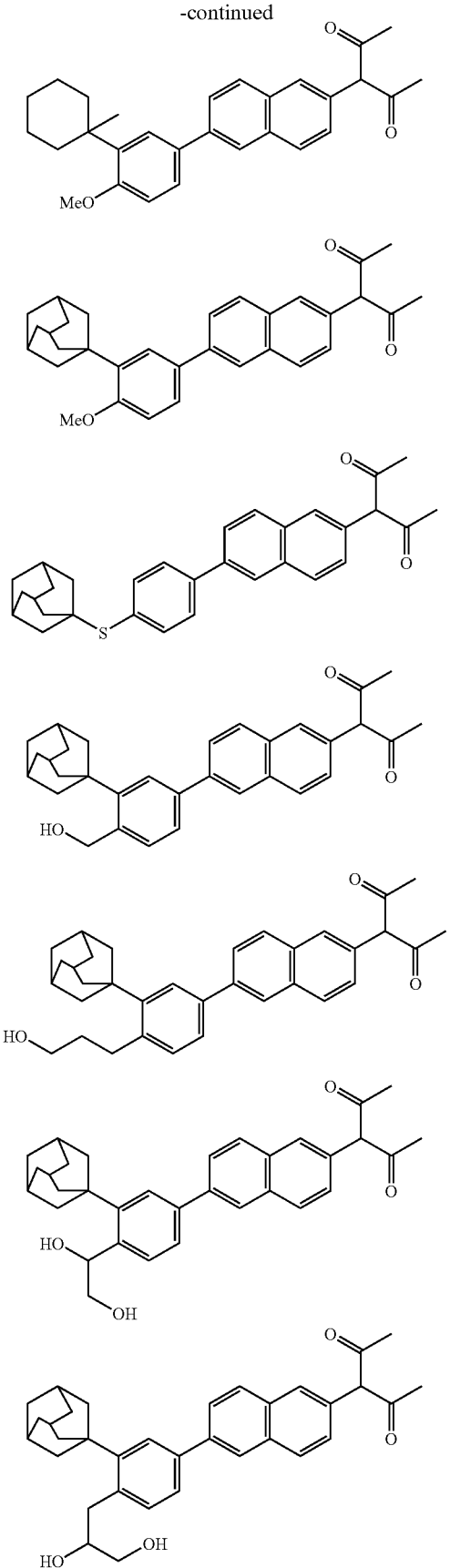

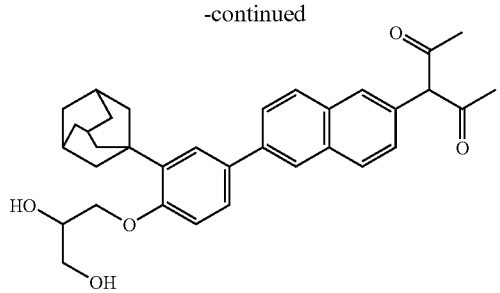

and pharmaceutically acceptable salts thereof.

Before the present compounds, compositions and methods are disclosed and described, it is to be understood that this invention is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a bicyclic aromatic compound" includes mixtures of bicyclic aromatic compounds, reference to "a pharmaceutical carrier" includes mixtures of two or more such carriers, and the like.

Certain pharmaceutically acceptable salts of the invention can be prepared by treating the novel compounds of the invention with an appropriate amount of pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water, alone or in combination with an inert, water-miscible organic solvent, at a temperature of from about 0° C. to about 100° C., preferably at room temperature. The molar ratio of compounds of structural formula A to base used is chosen to provide the ratio desired for any particular salts. For preparing, for example, the ammonium salts of the starting material, compounds of formula A can be treated with approximately one equivalent of the pharmaceutically acceptable base to yield a neutral salt. When calcium salts are prepared, approximately one-half a molar equivalent of base is used to yield a neutral salt, while for aluminum salts, approximately one-third a molar equivalent of base will be used.

The compounds of the invention according to formula A, including the pharmacologically acceptable pro-drugs or salts thereof, can be useful to elicit, modulate and/or regulate selective gene expression by cellular receptors and provide control over cellular growth, proliferation and differentiation processes regulated by certain hormones or vitamins such as for example all-trans-retinoic acid, 13-cis-retinoic acid, 9-cis-retinoic acid, vitamin D, thyroid hormone and the like. As noted above, the compounds of the invention are thus useful in the treatment of conditions and/or diseases that are regulated by the aforementioned entities. Examples of such conditions include for example cancer, mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia, acne, psoriasis, aging, wrinkling, diabetes, hyperglycemia, bone calcification, thyroid conditions, and the like The compounds of the invention may be conveniently formulated into pharmaceutical compositions composed of one or more of the compounds together with a pharmaceutically acceptable carrier as described in Remington's Pharmaceutical Sciences, latest edition, by E. W. Martin (Mack Publ. Co., Easton Pa.).

The compounds of the invention may be administered orally, parenterally (e.g., intravenously), by intramuscular injection, by intraperitoneal injection, topically, transdermally, or the like, although oral or topical administration is typically preferred. The amount of active compound administered will, of course, be dependent on the subject being treated, the subject's weight, the manner of administration and the judgment of the prescribing physician. The dosage will be in the range of about 2 microgram per kilogram per day to 10 milligram per kilogram per day.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels and the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents and the like.

For solid compositions, conventional non-toxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable-compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, fine powders or granules may contain diluting, dispersing, and/or surface active agents, and may be presented in water or in a syrup, in capsules or sachets in the dry state, or in a non-aqueous solution or suspension wherein suspending agents may be included, in tablets wherein binders and lubricants may be included, or in a suspension in water or a syrup. Wherever required, flavoring, preserving, suspending, thickening, or emulsifying agents may also be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, as emulsions, or as sustained release delivery system.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be through nasal sprays, for example, or using suppositories.

For topical administration, the agents can be formulated into ointments, creams, salves, powders and gels. In one aspect, the transdermal delivery agent can be DMSO. Transdermal delivery systems can include, such as for example, patches. Topical administration is particularly useful for use of the compound in the treatment of acne or psoriasis.

EXAMPLES

Used herein, the following abbreviations have the following meanings: Me refers to methyl ($CH_3$—), Et refers to ethyl ($CH_3CH_2$—), i-Pr refers to isopropyl (($CH_3$)$_2CH_2$—), t-Bu or tert-butyl refers to tertiary butyl (($CH_3$)$_3CH$—), Ph refers to phenyl, Bn refers to benzyl ($PhCH_2$—), Bz refers to benzoyl (PhCO—), MOM refers to methoxymethyl, Ac refers to acetyl, TMS refers to trimethylsilyl, TBS refers to ter-butyldimethylsilyl, Ms refers to methanesulfonyl ($CH_3SO_2$—), Ts refers to p-toluenesulfonyl (p-$CH_3PhSO_2$—), Tf refers to trifluoromethanesulfonyl ($CF_3SO_2$—), TfO refers to trifluoromethanesulfonate ($CF_3SO_3$—), DMF refers to N,N-dimethylformamide, DCM refers to dichloromethane ($CH_2Cl_2$), THF refers to tetrahydrofuran, EtOAc refers to ethyl acetate, $Et_2O$ refers to diethyl ether, MeCN refers to acetonitrile ($CH_3CN$), NMP refers to 1-N-methyl-2-pyrrolidinone, DMA refers to N,N-dimethylacetamide, DMSO refers to dimethylsulfoxide, DCC refers to 1,3-dicyclohexyldicarbodiimide, EDCI refers to 1-(3-dimethylaminopropyl)-3-ethylcarbodiimide, Boc refers to tert-butylcarbonyl, Fmoc refers to 9-fluorenylmethoxycarbonyl, TBAF refers to tetrabutylammonium fluoride, TBAI refers to tetrabutylammonium iodide, TMEDA refers to N,N,N,N-tetramethylethylene diamine, Dess-Martin periodinane or Dess Martin reagent refers to 1,1,1-triacetoxy-1,1-dihydro-1,2-benziodoxol-3(1H)-one, DMAP refers to 4-N,N-dimethylaminopyridine, (i-Pr)$_2$NEt or DIEA or Hunig's base refers to N,N-diethylisopropylamine, DBU refers to 1,8-Diazabicyclo[5.4.0]undec-7-ene, (DHQ)$_2$AQN refers to dihydroquinine anthraquinone-1,4-diyl diether, (DHQ)$_2$PHAL refers to dihydroquinine phthalazine-1,4-diyl diether, (DHQ)$_2$PYR refers to dihydroquinine 2,5-diphenyl-4,6-pyrimidinediyl diether, (DHQD)$_2$AQN refers to dihydroquinidine anthraquinone-1,4-diyl diether, (DHQD)$_2$PHAL refers to dihydroquinidine phthalazine-1,4-diyl diether, (DHQD)$_2$PYR refers to dihydroquinidine 2,5-diphenyl-4,6-pyrimidinediyl diether, LDA refers to lithium diisopropylamide, LiTMP refers to lithium 2,2,6,6-tetramethylpiperdinamide, n-BuLi refers to n-butyllithium, t-BuLi refers to tert-butyl lithium, IBA refers to 1-hydroxy-1,2-benziodoxol-3(1H)-one 1-oxide, $OsO_4$ refers to osmium tetroxide, m-CPBA refers to meta-chloroperbenzoic acid, DMD refers to dimethyl dioxirane, PDC refers to pyridinium dichromate, NMO refers to N-methyl morpholine-N-oxide, NaHMDS refers to sodium hexamethyldisilazide, LiHMDS refers to lithium hexamethyldisilazide, HMPA refers to hexamethylphosphoramide, TMSCl refers to trimethylsilyl chloride, TMSCN refers to trimethylsilyl cyanide, TBSCl refers to tert-butyldimethylsilyl chloride, TFA refers to trifluoroacetic acid, TFAA refers to trifluoroacetic anhydride, AcOH refers to acetic acid, $Ac_2O$ refers to acetic anhydride, AcCl refers to acetyl chloride, TsOH refers to p-toluenesulfonic acid, TsCl refers to p-toluenesulfonyl chloride, MBHA refers to 4-methylbenzhydrylamine, BHA refers to benzhydrylamine, $ZnCl_2$ refers to zinc (II) dichloride, $BF_3$ refers to boron trifluoride, $Y(OTf)_2$ refers to yttrium (III) trifluoromethanesulfonate, $Cu(BF_4)_2$ refers to copper (II) tetrafluoroborate, LAH refers to lithium aluminum hydride ($LiAlH_4$), $NaHCO_3$ refers to sodium bicarbonate, $K_2CO_3$ refers to potassium carbonate, NaOH refers to sodium hydroxide, KOH refers to potassium hydroxide, LiOH refers to lithium hydroxide, HCl refers to hydrochloric acid, $H_2SO_4$ refers to sulfuric acid, $MgSO_4$ refers to magnesium sulfate, and $Na_2SO_4$ refers to sodium sulfate. 1H NMR refers to proton nuclear magnetic resonance, 13C NMR refers to carbon 13 nuclear magnetic resonance, NOE refers to nuclear overhauser effect, NOESY refers to nuclear overhauser and exchange spectroscopy, COSY refers to homonuclear correlation spectroscopy, HMQC refers to proton detected heteronuclear multiplet-quantum coherence, HMBC refers to heteronuclear multiple-bond connectivity, s refers to singlet, br s refers to broad singlet, d refers to doublet, br d refers to broad doublet, t refers to triplet, q refers to quartet, dd refers to double doublet, m refers to multiplet, ppm refers to parts per million, IR refers to infrared spectrometry, MS refers to mass spectrometry, HRMS refers to high resolution mass spectrometry, EI refers to electron impact, FAB refers to fast atom bombardment, CI refers to chemical ionization, HPLC refers to high pressure liquid chromatography, TLC refer to thin layer chromatography, $R_f$ refers to, $R_t$ refers to retention time, GC refers to gas chromatography, min is minutes, h is hours, rt or RT is room temperature, g is grams, mg is milligrams, L is liters, mL is milliliters, mol is moles and mmol is millimoles.

For all of the following examples, standard work-up and purification methods can be utilized and will be obvious to those skilled in the art. Synthetic methodologies that make up the invention are shown in Schemes 1-2. These Schemes are intended to describe the applicable chemistry through the use of specific examples and are not indicative of the scope of the invention.

Example 1

1-(5-Bromo-2-methoxyphenyl)-adamantane

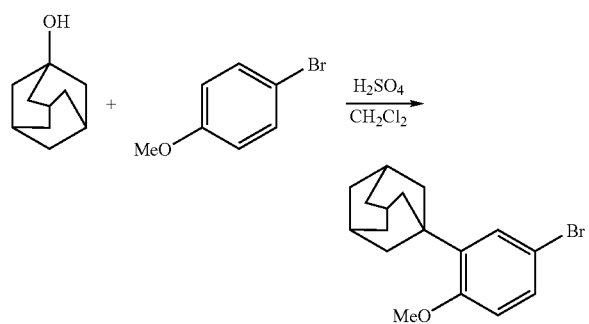

Reagent grade concentrated $H_2SO_4$ (11 mL) was added dropwise to a solution of 1-adamantol (30.25 g, 200 mmol) and 4-bromoanisole (37.21 g, 200 mmol) in 130 mL of $CH_2Cl_2$. The light pink solution was stirred at ambient temperature for 20 hours. The solvent was decanted, water (100 mL) and hexane (100 mL) were added and the solid was filtered and washed with hexane and dried to give 31 g of the product as a white powder. The supernatant was diluted with hexane, washed with water and brine, dried over $MgSO_4$ and filtered thru a silica gel pad. The solvent was removed and the solid was recrystallized from hexane to yield 17 g of the product as a white powder.

Yield: 65 g (75%); white solid; $R_f$=0.9 in 25% EtOAc-hexane. $^1$H NMR ($CDCl_3$, 300 MHz) δ 1.78 (s, 6H), 2.08 (s, 9H), 3.81 (s, 3H), 6.72 (d, 1H), 7.24 (dd, 1H), 7.28 (m, 1H)

Example 2

1-(5-Boronic acid-2-methoxyphenyl)-adamantane

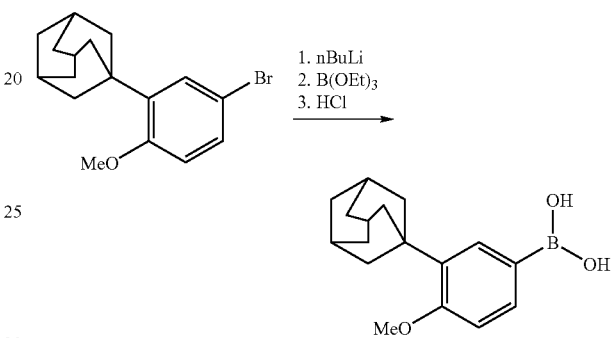

To a solution of 1-(5-bromo-2-methoxyphenyl)-adamantane (4 g, 12.5 mmol) in 40 mL of THF was added a 2.5M solution of n-BuLi in hexane (5 mL, 12.5 mmol) at −78° C., under nitrogen. The mixture was stirred for 5 minutes at −78° C., triethylborate (1.88 g, 12.9 mmol) was added and the mixture was stirred for an additional 30 minutes at −78° C. The reaction was allowed to slowly warm to room temperature and was quenched by addition of 1N HCl (30 mL). The mixture was diluted with $Et_2O$, washed with water and brine, dried over $Na_2SO_4$, filtered thru a pad of silica gel and the solvent was removed to yield the crude product which was recrystallized from chloroform.

Yield: 0.45 g (12%); white solid; $^1$H NMR ($CDCl_3$-MeOD 10:1, 300 MHz) δ 1.74 (s, 6H), 2.08 (m, 9H), 2.9 (s, 2H), 3.81 (s, 3H), 6.82 (d, 1H), 7.52 (m, 2H)

Example 3

2-tert-Butyl-dimethylsilanoxy-6-bromo-naphthalene

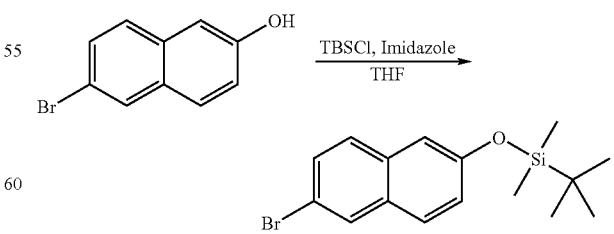

To a solution of 6-bromo-2-napthol (1.12 g, 5 mmol) in anhydrous THF (15 mL) was added imidazole (0.476 g, 7 mmol) followed by TBSCl (1.05 g, 7 mmol) at room temperature under nitrogen atmosphere. The reaction mixture was stirred at room temperature for 40 h and was diluted with ether, washed with brine and dried over anhydrous Mg$_2$SO$_4$. The solvent was removed to yield the crude product, which was recrystallized from methanol.

Yield: 1.36 g (80%), white crystals. 1H-NMR (CDCl$_3$) δ 0.08 (s, 6H), 1.06 (s, 9H), 7.08 (dd, 1H), 7.15 (s, 1H), 7.47 (dd, 1H), 7.56 (d, 1H), 7.64 (d, 1H), 7.92 (s, 1H)

Example 4

2-tert-Butyl-dimethylsilanoxy-6-boronic acid-naphthalene

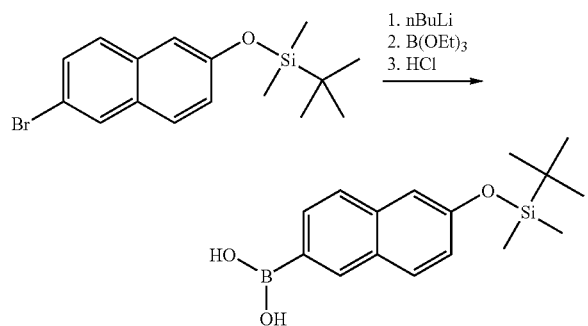

Prepared according to example 2, starting with 30 g of the bromide. The crude product was recrystallized from hexane.

Yield: 24 g (89%), white solid. 1H-NMR (CDCl$_3$) δ 0.3 (s, 6H), 1.05 (s, 9H), 7.16 (dd, 1H), 7.26 (m, 1H), 7.82 (d, 1H), 7.98 (d, 1H), 8.24 (dd, 1H), 8.8 (s, 1H)

Example 5

2-tert-Butyl-dimethylsiloxy 6-(3-adamantan-1-yl-4-methoxyphenyl)-naphthalene

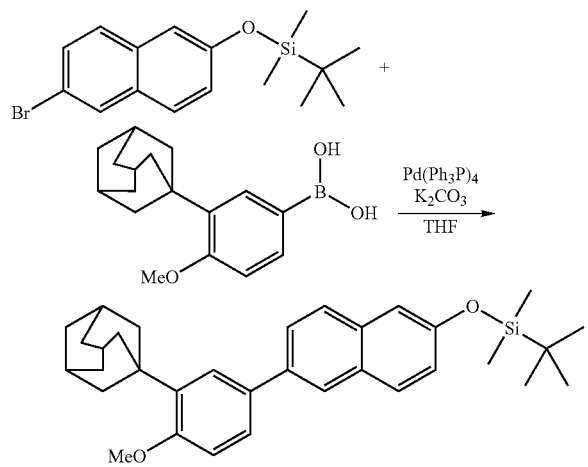

1-(5-Boronic acid-2-methoxyphenyl)-adamantane (429 mg, 1.5 mmol), 2-tert-butyl-dimethylsilanoxy-6-bromo-naphthalene (337 mg, 1 mmol) and palladium tetrakis(triphenylphosphine) (58 mg, 0.05 mmol) were placed in a Schlenk flask and the vessel flushed with nitrogen. Degassed THF (3 mL) and degassed 1 M aqueous K$_2$CO$_3$ (2.5 mL) were added to the reaction flask and the mixture was placed in a 70° C. bath and stirred under nitrogen for 3.5 hours. The reaction was cooled to room temperature and the layers were separated. The organic layer was dried over Na$_2$SO$_4$ and filtered thru a short pad of silica gel. The solvent was removed to yield the product.

Yield: 0.45 g (90%); white solid; R$_f$=0.7 in 25% EtOAc-hexane. $^1$H NMR (CDCl$_3$, 300 MHz) δ 0.3 (s, 6H), 1.05 (s, 9H), 1.72 (s, 6H), 2.2 (s, 3H), 2.4 (s, 6H), 3.81 (s, 3H), 6.98 (d, 1H), 7.09 (dd, 1H), 7.2 (d, 1H), 7.5 (dd, 1H), 7.56 (d, 1H), 7.66 (dd, 1H), 7.75 (m, 2H), 7.9 (d, 1H)

Example 6

2-tert-Butyl-dimethylsiloxy 6-(3-adamantan-1-yl-4-methoxyphenyl)-naphthalene

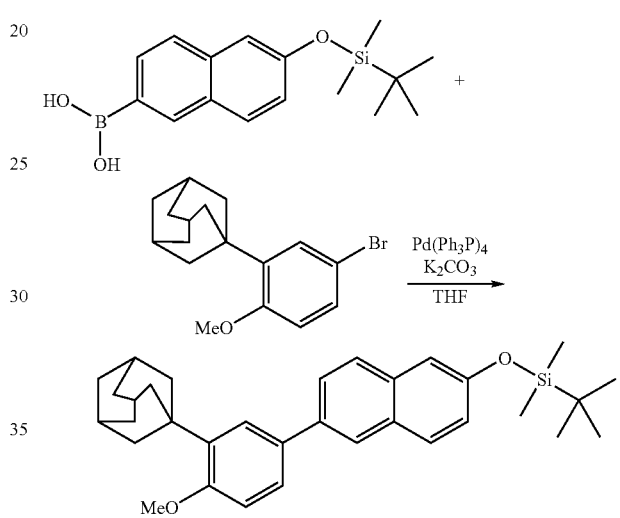

Prepared according to example 5, starting with 5.8 g of the bromide. The crude product was filtered thru a short pad of silica gel. Yield: 7.7 g (85%); white solid; R$_f$=0.7 in 25% EtOAc-hexane.

Example 7

Toluene-4-sulfonic acid 6-(3-adamantan-1-yl-4-methoxyphenyl)-naphthalen-2-yl ester

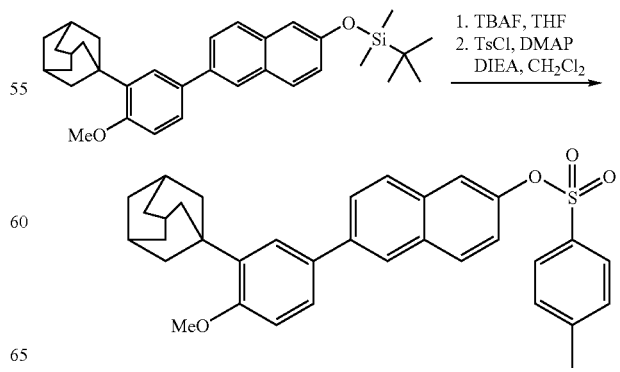

To a solution of 2-tert-butyl-dimethylsiloxy-6-(3-adamantan-1-yl-4-methoxyphenyl)-naphthalene (14 g, 28 mmol) in THF (160 ml) was added TBAF (28 ml, 28 mmol) and the reaction stirred at RT for 5 min. The reaction mixture was diluted with EtOAc and washed with 1N HCl, brine, and dried over Na$_2$SO$_4$. The crude product was concentrated in vacuo and the residue was dissolved in DCM (200 ml). DMAP (0.2 equiv), DIEA (1.2 equiv) and toluene-4-sulfonyl chloride (1 equiv) were added and the reaction was stirred at RT for 30 minutes. The solvent was removed, the residue was dissolved in EtOAc, washed with 1N HCl, brine, and dried over Na$_2$SO$_4$. The solvent was removed and the crude product was recrystallized from acetonitrile.

Yield: 12.2 g (81%); R$_f$=0.65 in 25% EtOAc-hexane. $^1$H NMR (CDCl$_3$, 300 MHz) δ 1.81 (s, 6H), 2.11 (s, 3H), 2.19 (s, 6H), 3.91 (s, 3H), 6.98 (d, 1H), 7.09 (dd, 1H), 7.3 (m, 2H), 7.52 (m, 3H), 7.75 (m, 5H), 7.94 (s, 1H)

Example 8

2-[6-(3-Adamantan-1-yl-4-methoxyphenyl)-naphthalen-2-yl]-3-hydroxy-cyclopent-2-enone

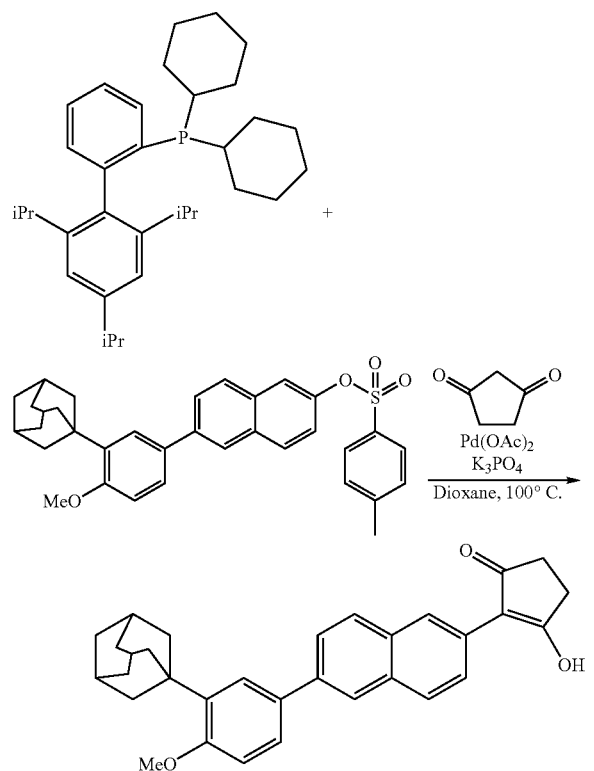

A flame-dried Schlenk tube containing a Teflon coated stir bar was charged with Pd(OAc)$_2$ (20 mg, 0.088 mmol), (2-dicyclohexylphosphino)-2',4',6'-triisopropyl biphenyl (105 mg, 0.22 mmol), 1,3-cyclopentanedione (65 mg, 0.66 mmol), toluene-4-sulfonic acid 6-(3-adamantan-1-yl-4-methoxyphenyl)-naphthalen-2-yl ester (238 mg, 0.44 mmol) and finely ground K$_3$PO$_4$ (233 mg, 1.1 mmol). The tube was capped with a septum, evacuated and backfilled with nitrogen three times, 2 mL of dry dioxane was injected and the mixture was heated to 100° C. for 3 h. The mixture was then cooled, diluted with EtOAc, washed with 1N HCl, dried over Na$_2$SO$_4$ and filtered. The filtrate was concentrated and purified by flash chromatography using MeOH—CH$_2$Cl$_2$.

Yield: 184 mg (90%); R$_f$=0.3 in 10% MeOH—CH$_2$Cl$_2$. $^1$H NMR (MeOD-CDCl$_3$ (1:8), 300 MHz) δ 1.73 (s, 6H), 2.02 (s, 3H), 2.11 (s, 6H), 2.58 (s, 4H), 3.81 (s, 3H), 6.89 (d, 1H), 7.44 (dd, 1H), 7.50 (d, 1H), 7.5 (dd, 1H), 7.6 (dd, 1H), 7.78 (m, 2H), 7.85 (m, 2H), 8.19 (s, 1H)

Example 9

Topical Gel

Combination of the active principle with propylene glycol, carbomer 940, poloxamer 182, edetate disodium, methylparaben, sodium hydroxide, hydrochloric acid and purified water. The amount of the active principle may be 0.001 to 10 weight percent based on the total weight of said composition. An example of an active principle is 2-[6-(3-adamantan-1-yl-4-methoxyphenyl)-naphthalen-2-yl]-3-hydroxy-cyclopent-2-enone.

Example 10

Topical Gel

Combination of the active principle with butylated hydroxytoluene, hydroxypropyl cellulose, polyolprepolymer-2, and ethanol (denatured with tert-butyl alcohol and brucine sulfate) 83% w/w. The amount of the active principle may be 0.001 to 10 weight percent based on the total weight of said composition. An example of an active principle is 2-[6-(3-adamantan-1-yl-4-methoxyphenyl)-naphthalen-2-yl]-3-hydroxy-cyclopent-2-enone.

Example 11

Topical Gel

Combination of the active principle with ascorbic acid, butylated hydroxyanisole, butylated hydroxytoluene, carbomer 934P, edetate disodium, hexylene glycol, purified water, poloxamer 407, polyethylene glycol 400, polysorbate 40, and tromethamine. The amount of the active principle may be 0.001 to 10 weight percent based on the total weight of said composition. An example of an active principle is 2-[6-(3-adamantan-1-yl-4-methoxyphenyl)-naphthalen-2-yl]-3-hydroxy-cyclopent-2-enone.

Example 12

Topical Cream

Combination of the active principle with stearic acid, polyolprepolymer-2, isopropyl myristate, polyoxy 40 stearate, propylene glycol, stearyl alcohol, xanthan gum, sorbic acid, butylated hydroxytoluene, and purified water. The amount of the active principle may be 0.001 to 10 weight percent based on the total weight of said composition. An example of an active principle is 2-[6-(3-adamantan-1-yl-4-methoxyphenyl)-naphthalen-2-yl]-3-hydroxy-cyclopent-2-enone.

Example 13

Topical Cream

Combination of the active principle with Cetearyl octanoate, glycerin, glyceryl stearate, cetearyl alcohol, cetyl palmitate, cocoglycerides, PEG-5 glyceryl stearate, propylene glycol, and purified water. The amount of the active principle may be 0.001 to 10 weight percent based on the total weight of said composition. An example of an active principle is 2-[6-(3-adamantan-1-yl-4-methoxyphenyl)-naphthalen-2-yl]-3-hydroxy-cyclopent-2-enone.

Example 14

Topical Cream

Combination of the active principle with carbomer 934P, cyclomethicone, edetate disodium, glycerin, methyl glucose sesquistearate, methyl paraben, PEG-20 methyl glucose sesquistearate, phenoxyethanol, propylparaben, purified water, squalene, and trolamine. The amount of the active principle may be 0.001 to 10 weight percent based on the total weight of said composition. An example of an active principle is 2-[6-(3-adamantan-1-yl-4-methoxyphenyl)-naphthalen-2-yl]-3-hydroxy-cyclopent-2-enone.

The compounds of this invention are novel therapeutic agents for the treatment of cancer, metabolic diseases and skin disorders in mammalian subjects. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

Example 15

RAR-α Expression

The Plasmid pGEG-hRAR-α for full-length RAR-α expression was transformed into *E. coli* BL21 (DE3). A single colony was picked and inoculated in LB medium with ampicillin (100 μg/ml). The culture was grown at 37° C. until cell density corresponding to an $OD_{600}$ of 0.7 was reached. Isopropyl β-D thiogalactopyranoside (IPTG) was added to 1 mM to induce RAR-α protein. Induction continued for overnight at 25° C. and cells were collected by centrifugation. The cell pellet was then resuspended in 10% of the original volume of the lysis buffer (20 mM Tris, pH 7.8, 150 mM KCl, 5% Triton X100, 0.2 mM PMSF (added just before use) and 1 mM dithiothreitol (DTT added just before use)). Cells were lysed by five cycles of freezing/thawing in EtOH/dry ice bath and 5 times pulse sonication. Centrifugation at 20,000 rpm was performed to separate soluble proteins from cell debris. The supernatant was saved and used for subsequent protein purification.

Example 16

RAR-α Purification 10 mL of Glutathione Sepharose 4B was packed in a chromatography column and washed with 100 mL of PBS (140 mM NaCl, 2.7 mM KCl, 10 mM $Na_2HPO_4$, 1.8 mM $KH_2PO_4$) to remove the preservatives. The gel was equilibrated with 30 mL of PBS. The RAR-α sample was filtered through a 0.45 μm filter before applying to the column. The sample was applied to the column and the eluent was discarded. The column was washed with 100 mL of PBS. The bound RAR-α was eluted with 50 mL of elution buffer (10 mM Glutathione in 50 mM Tris-HCl pH 8.0) and fractions (11×4 mL) were collected. Protein gel electrophoresis was used to analyze protein samples (eleven collected fractions) under denaturing conditions. See FIGS. 1 and 2 for fractions 1-6 and 7-11, respectively. See also FIG. 3 for comparison of the results of gel electrophoresis separation of various fractions.

Example 17

Binding Assay

The hydroxylapatite binding method was used the hormone and compounds binding activity of RAR-α. A desired amount of tritium labeled all-trans-retinoic acid (tRA) (5 nM) was dried down to evaporate trace of ethanol and mixed thoroughly with 10 μL of 0.5 mg/mL RAR-α (5 μg) protein and binding buffer (120 mM KCl, 8 mM Tris phosphate, pH 7.4, 8% glycerol, 4 mM dithiothreitol, 0.5% CHAPS detergent and 0.24 mM phenylmethylsulfonyl fluoride). The final volume was 250 μL. To determine non-specific binding, 200-fold molar excess of unlabeled tRA was mixed with tritium labelled tRA before addition of the RAR-α protein. Incubation was carried out at 4° C. for 18 hours in the dark. The specific binding to receptor was determined by a hydroxylapatite (HAP) separation method. HAP slurry (50% in 100 mM KCl, 10 mM Tris phosphate, pH 7.4; 100 μL) was added to each tube and vortexed every 10 min for 40 min at 4° C. The suspension was centrifuged for 5 min at 2000×g, and the pellet was washed three times with cold buffer containing 100 mM KCl, 10 mM Tris phosphate, pH 7.4, 0.5% CHAPS. The HAP pellet was resuspended in 150 μL wash buffer, then in 1 mL of ULTIMA GOLD liquid scintillation cocktail. The amount of receptor-ligand complex was determined by liquid scintillation counting. After correcting for non-specific binding, $IC_{50}$ values were determined. $K_d$ values for compounds were calculated by application of the Cheng-Prussoff equation, $K_d=IC_{50}/(1+L/K_L)$, where L is the concentration of free radioligand and $K_L$ is the equilibrium dissociation constant of the radioligand. Measured $K_L$ for tRA is 3.375 μM. Exemplary competitive binding data are shown in Table 1 and illustrated in FIGS. 4 and 5.

TABLE 1

| Competitive Binding Data in *E. Coli* Expressed RAR-α ||
| Compound | $K_d$ (mircomolar) |
| --- | --- |
| Example 8 | 16 |
| Adapalene | 0.3 |

What is claimed is:

1. Compounds having the structural formula $C_1$:

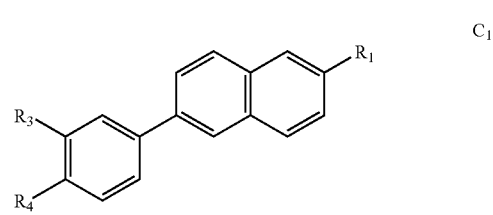

wherein:

$R_1$ is selected from a group consisting of the structural formulae $B_1$, $B_2$, and $B_3$,

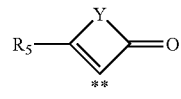

B1

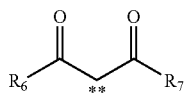

B2

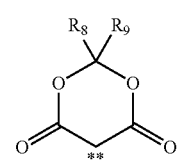

B3

$R_3$ is selected from a group consisting of hydrogen, alkyl, adamantyl, alkyloxy, alkylthio, halogen, aryl, aryloxy, arylthio, and heteroaryl;

$R_4$ is selected from a group consisting of hydrogen, hydroxy, alkyl, alkyloxy, alkylthio, aryl, aryloxy, arylthio and heteroaryl;

at least one of $R_3$ and $R_4$ is not hydrogen or halogen;

$R_5$ is —OH;

$R_6$ and $R_7$ are independently selected from the group consisting of alkyl, alkyloxy, —$NH_2$, and alkylamino;

$R_8$ and $R_9$ are independently selected from a group consisting of hydrogen and alkyl;

Y is selected from a group consisting of $C_{2-8}$ alkyl, and $C_{2-8}$ substituted alkyl;

where ** represents the point of attachment of $R_1$ to $R_2$ and pharmaceutically acceptable salts thereof.

2. A pharmaceutical composition comprising a pharmaceutically acceptable vehicle suitable for enteral, parenteral, topical or ocular administration and an effective amount of an active principle composed of at least one compound of claim 1 or a pharmaceutically acceptable salt thereof.

3. The pharmaceutical composition of claim 2 wherein said active principle is present in an amount ranging from 0.0001 to about 10 weight percent based on the total weight of said composition.

4. A pharmaceutical composition comprising a compound according to claim 1 together with one or more pharmaceutically acceptable carriers or diluents.

5. The pharmaceutical composition according to claim 4 in the form of an oral dosage unit or parenteral dosage unit.

6. Compounds selected from a group consisting of

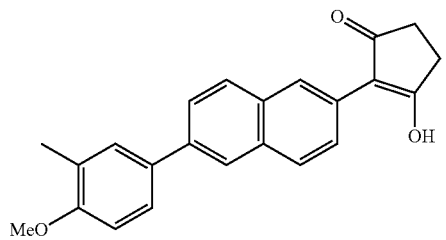

-continued

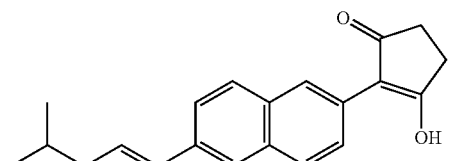

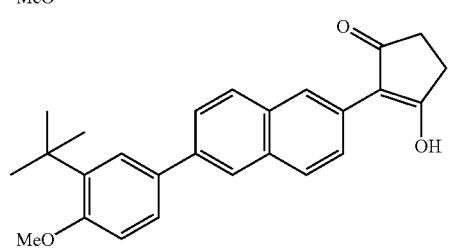

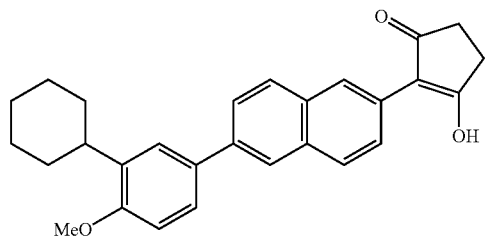

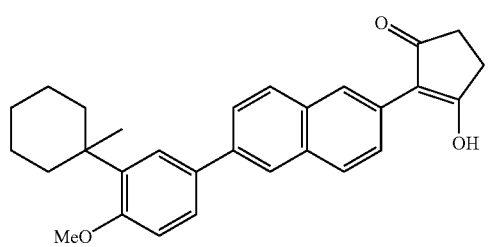

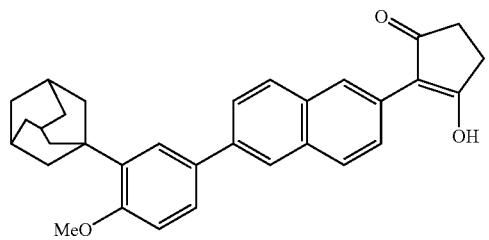

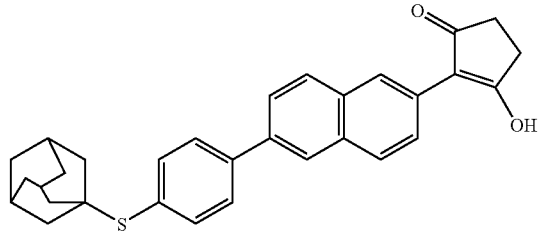

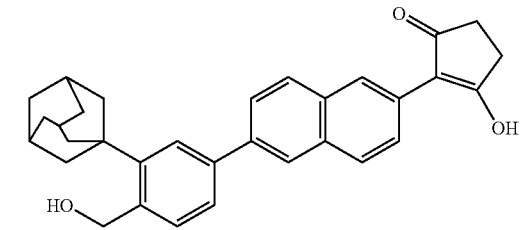

-continued
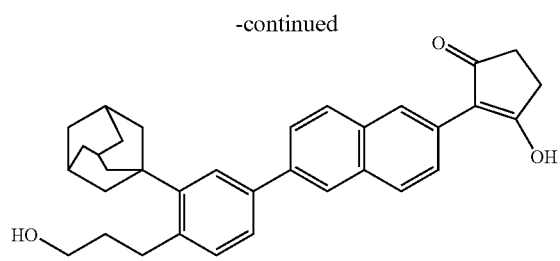
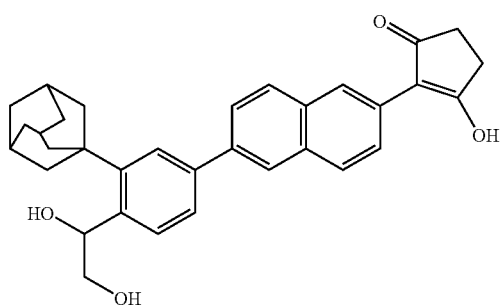
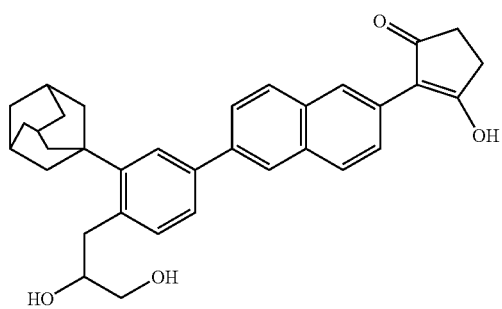
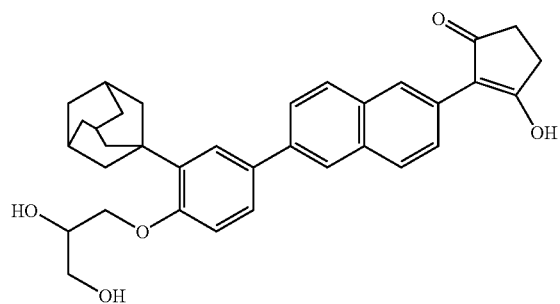
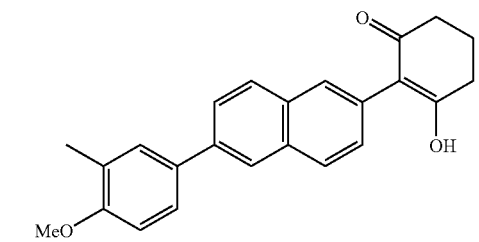
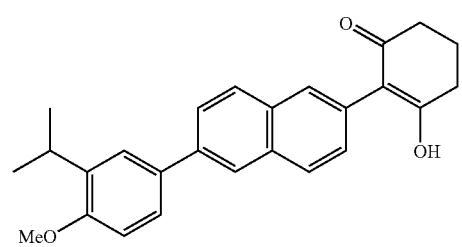
-continued
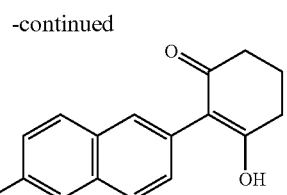
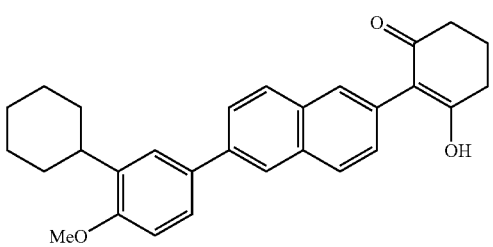
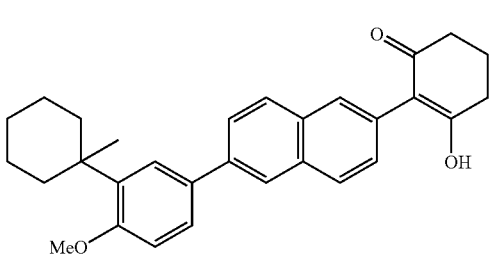
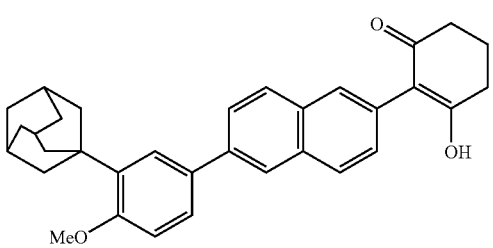
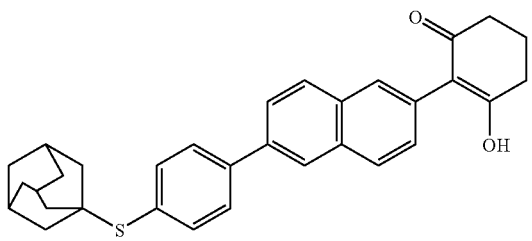
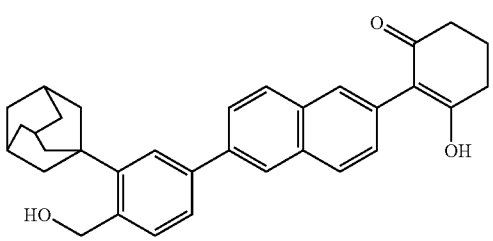

-continued
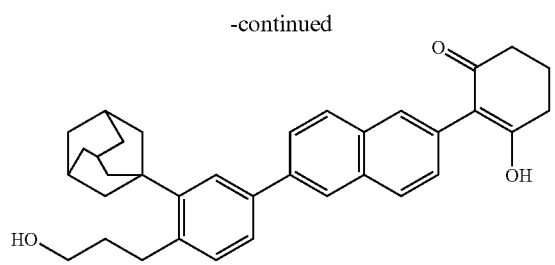
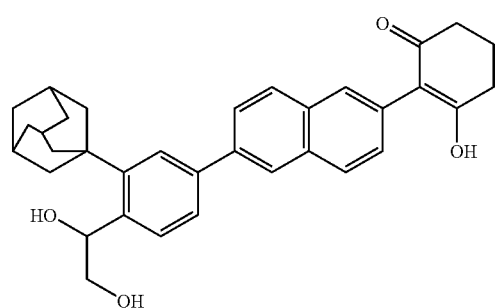
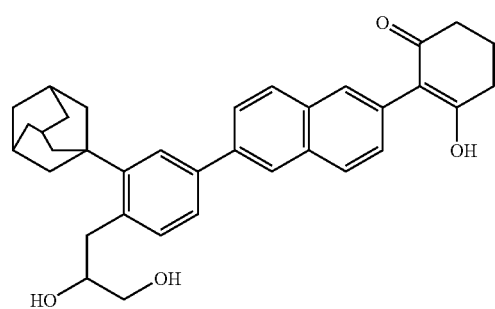
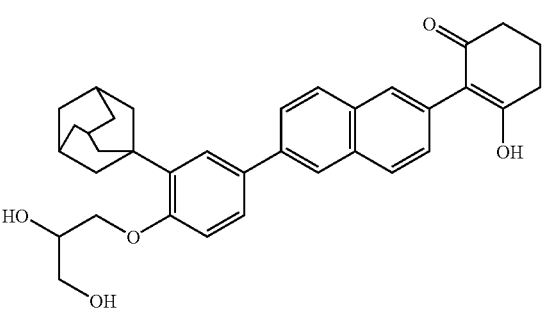
and pharmaceutically acceptable salts thereof.
7. Compounds selected from a group consisting of
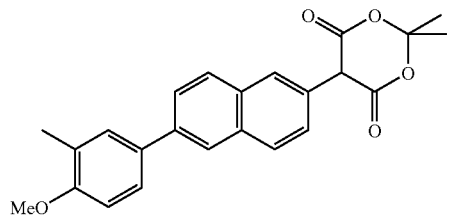
-continued
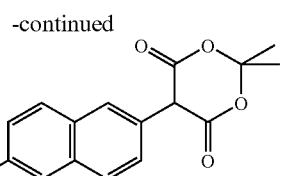
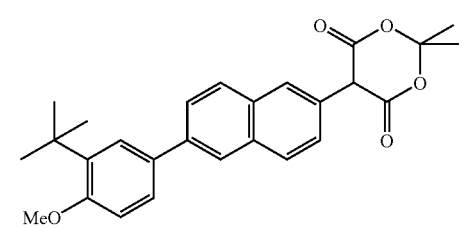
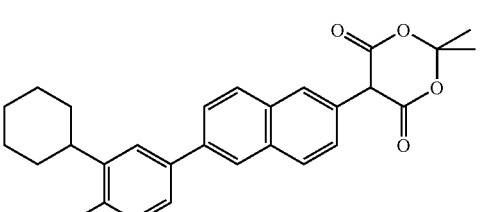
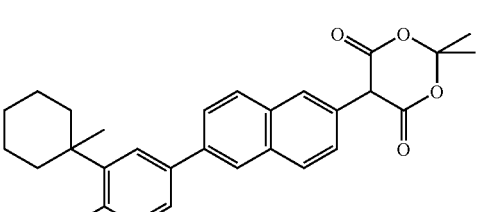
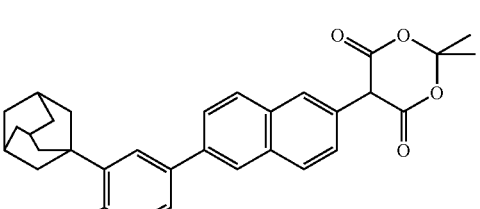
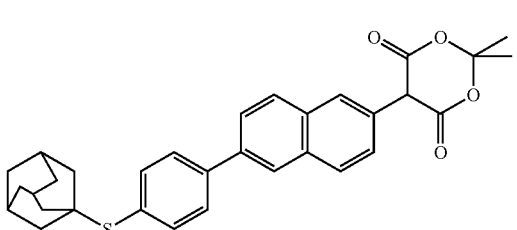
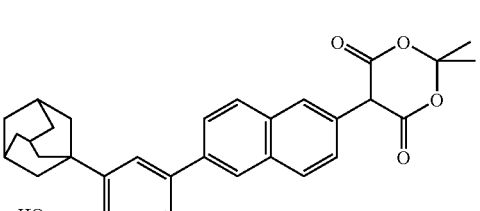

-continued
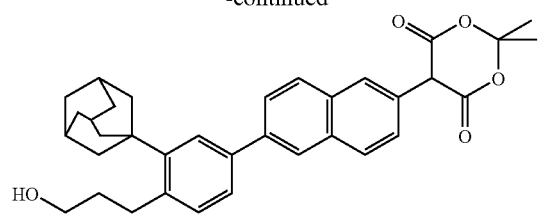
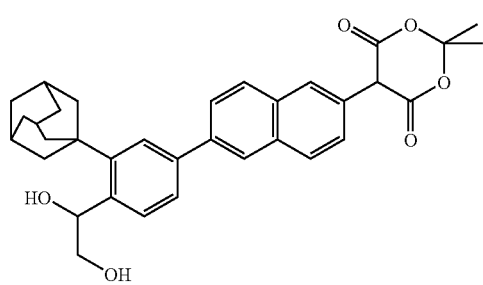
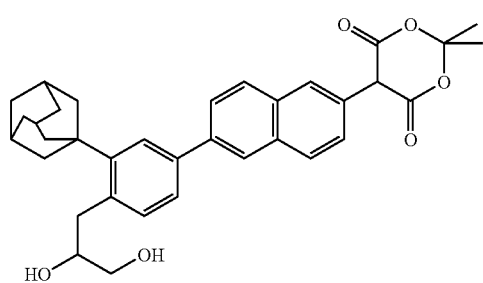
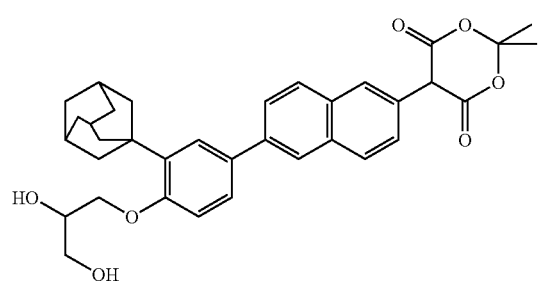
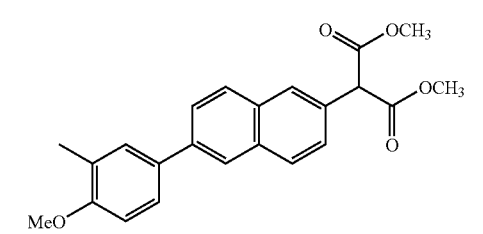
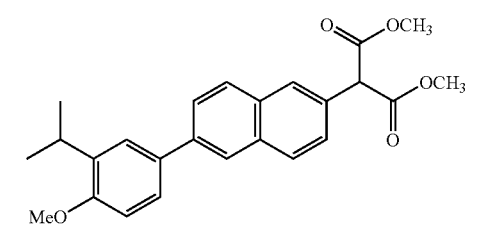
-continued
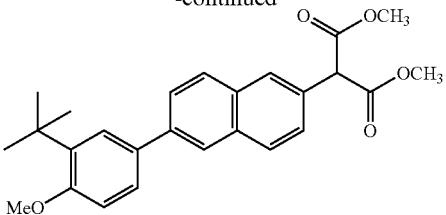
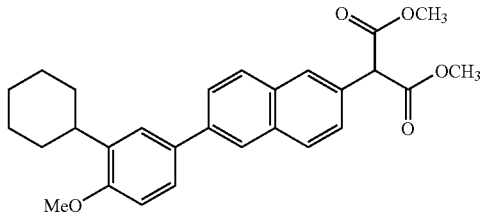
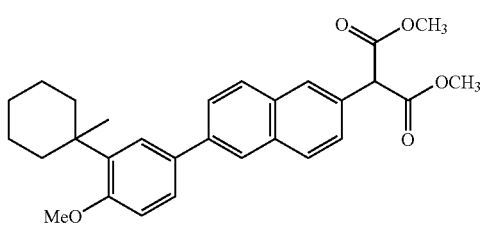
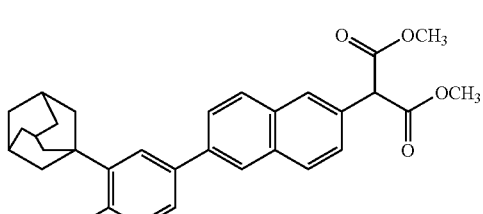
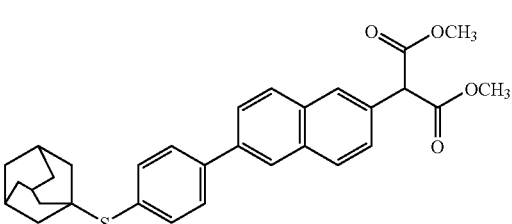
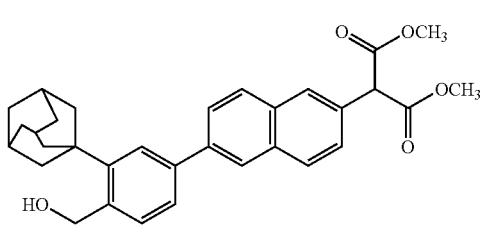
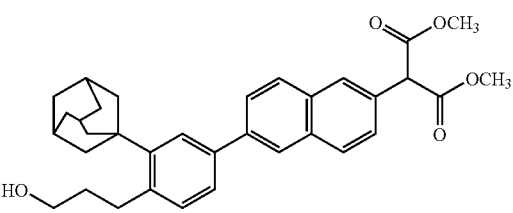

-continued
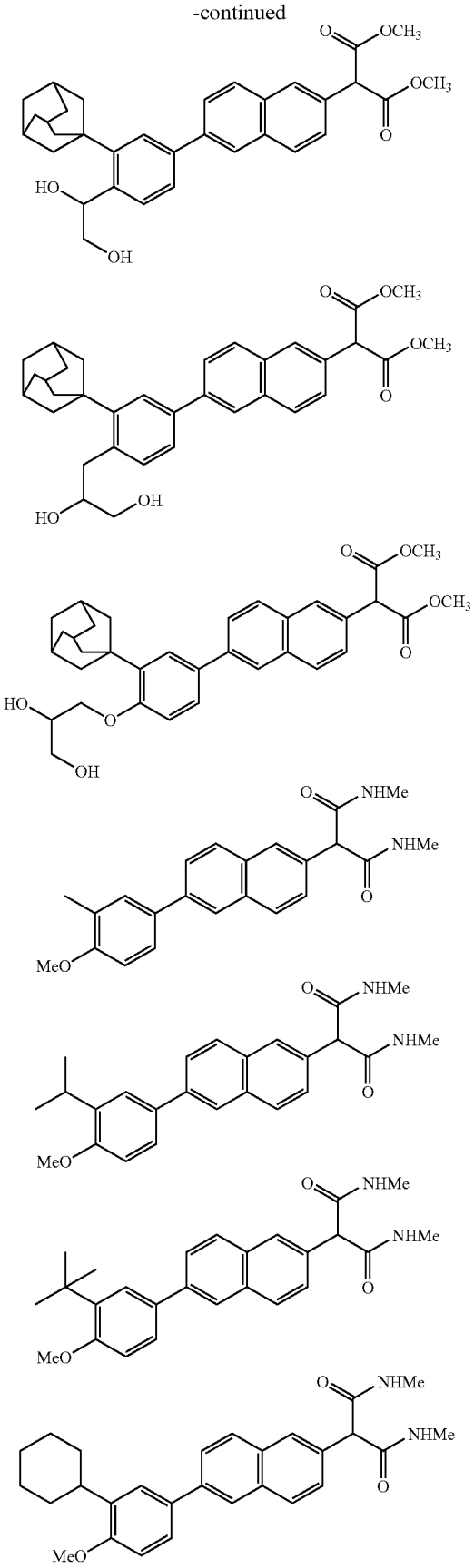
-continued
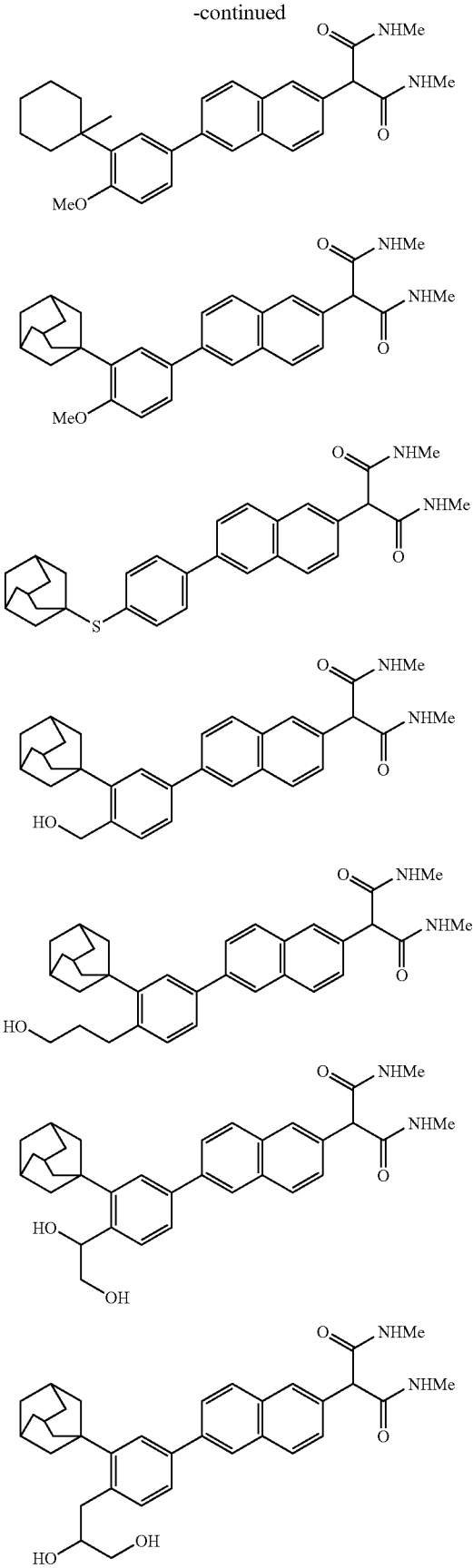

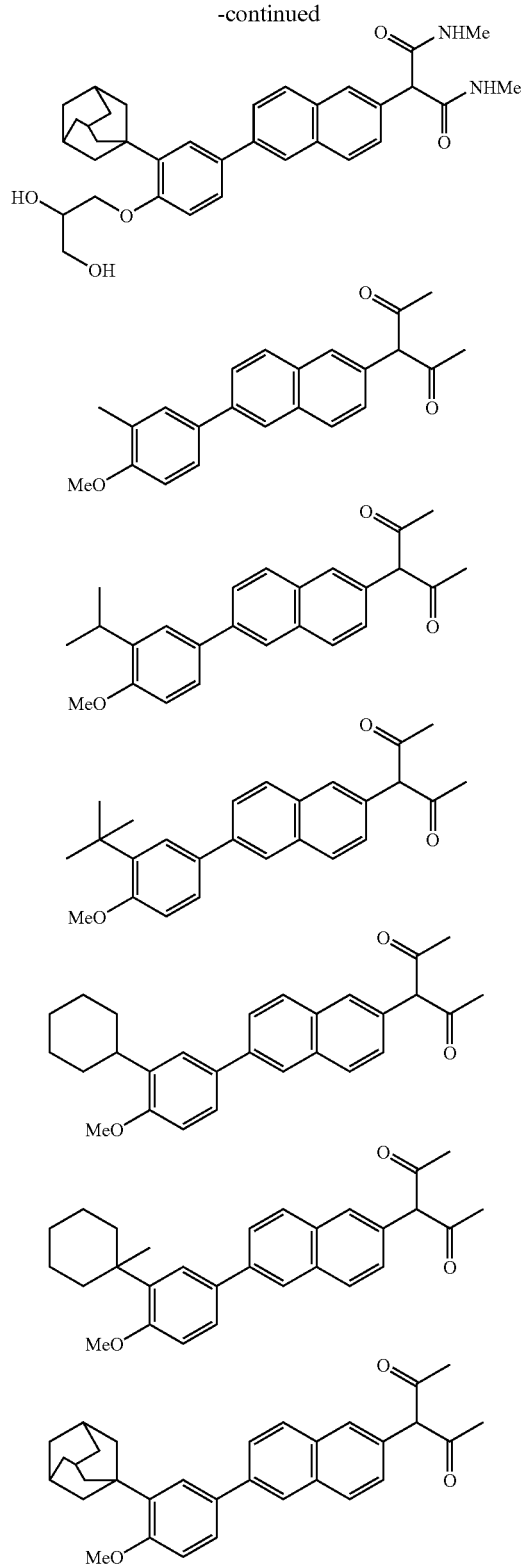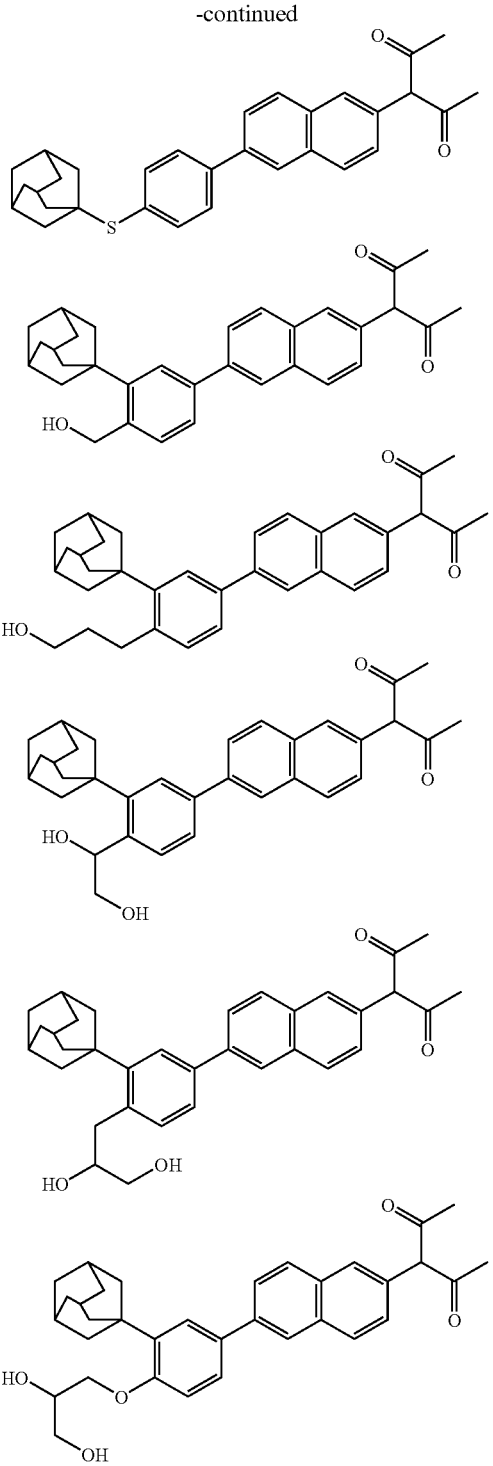
and pharmaceutically acceptable salts thereof.
* * * * *